(12) United States Patent
Pardoll et al.

(10) Patent No.: US 8,551,481 B2
(45) Date of Patent: Oct. 8, 2013

(54) ANTI-CANCER VACCINE COMPOSITION COMPRISING AN ANTI-CD223 ANTIBODY AND KIT COMPRISING AN ANTI-CANCER VACCINE AND AN ANTI-CD223 ANTIBODY

(75) Inventors: Drew M Pardoll, Brookeville, MD (US); Ching-Tai Huang, Taipei (TW); Jonathan Powell, Baltimore, MD (US); Charles Drake, Baltimore, MD (US); Dario A Vignali, Germantown, TN (US); Creg J Workman, Memphis, TN (US)

(73) Assignees: The Johns Hopkins University, Baltimore, MD (US); St. Jude Children's Research Hospital, Inc., Memphis, TN (US)

( * ) Notice: Subject to any disclaimer, the term of this patent is extended or adjusted under 35 U.S.C. 154(b) by 117 days.

(21) Appl. No.: 12/578,887

(22) Filed: Oct. 22, 2009

(65) Prior Publication Data

US 2010/0196394 A1 Aug. 5, 2010

Related U.S. Application Data

(63) Continuation of application No. 10/547,371, filed as application No. PCT/US2004/006133 on Mar. 1, 2004, now abandoned.

(60) Provisional application No. 60/531,704, filed on Dec. 22, 2003, provisional application No. 60/482,143, filed on Jun. 24, 2003, provisional application No. 60/451,039, filed on Feb. 28, 2003.

(51) Int. Cl.
| | |
|---|---|
| *A61K 39/00* | (2006.01) |
| *A61K 39/395* | (2006.01) |
| *A61K 39/38* | (2006.01) |
| *C12P 21/08* | (2006.01) |

(52) U.S. Cl.
USPC .................. 424/139.1; 424/141.1; 424/184.1; 530/388.1; 530/388.75

(58) Field of Classification Search
None
See application file for complete search history.

(56) References Cited

U.S. PATENT DOCUMENTS

| | | | |
|---|---|---|---|
| 4,658,957 | A | 4/1987 | Guth et al. |
| 5,773,578 | A | 6/1998 | Hercend et al. |
| 5,874,250 | A | 2/1999 | Hercend et al. |
| 5,955,300 | A | 9/1999 | Faure et al. |
| 5,976,877 | A | 11/1999 | Hercend et al. |
| 6,143,273 | A | 11/2000 | Faure et al. |
| 6,197,524 | B1 | 3/2001 | Romagnani |
| 6,410,509 | B1 | 6/2002 | Triebel |
| 6,432,925 | B1 | 8/2002 | Hoon et al. |
| 6,482,925 | B1 | 11/2002 | El Tayar et al. |
| 6,500,422 | B2 | 12/2002 | Biffoni et al. |
| RE38,313 | E | 11/2003 | Faure et al. |

FOREIGN PATENT DOCUMENTS

| | | |
|---|---|---|
| EP | 0900841 | 10/1999 |
| JP | 2000-508226 | 7/2000 |
| JP | 2002-505582 | 2/2002 |
| WO | 9703695 | 2/1997 |
| WO | 9823748 | 6/1998 |
| WO | 9858059 | 12/1998 |

OTHER PUBLICATIONS

Avice et al.: "Lymphocyte Activation Gene-3, a MHC Class II Ligand Expressed on Activated T Cells, Stimulates TNF-a and IL-12 Production by Monocytes and Dendritic Cells", The American Association of Immunologists, 1999, pp. 2748-2753.
Huard et al.: Characterization of the major histocompatibility complex class II binding site on LAG-3 protein, Proc.Natl.Acad.Sci. USA, vol. 94, pp. 5744-5749, May 1997 Immunology.
Hannier et al.: "CD3/TCR Complex-Associated Lymphocyte Activation Gene-3 Molecules INhibit CD3/TCR Signaling", The American Association of Immunologists, 1998, pp. 4058-4065.
Huard et al.: "Lymphocyte-activation gene 3/major histocompatibility complex class II interaction modulates the antigenic response of CD4+T lymphocytes", Eur J Immunol, Dec. 1994; 24 (12), 3216-21.
El Mir et al.: "A Soluble Lymphocyte Activation Gene-3 Molecule Used as a Vaccine Adjuvant Elicits Greater Humoral and Cellular Immune Responses to Both Particulate and Soluble Antigens", The Journalof Immunology, 2000, pp. 5583-5589.
Cappello et al.: "LAG-3 enables DNA vaccination to persistently prevent mammary carcinogenesis in HER-2/neu transgenic BALB/c mice", Cancer Res. May 15, 2003, 63 (10), 2518-25.
Workman et al.: "The CD4-related molecule, LAG-3 (CD223), regulates athe expansion of activated T cells", Eur J Immunol, Apr. 2003, 33 (4), 970-9.
Andreae et al.: "MHC class II signal transduction in human dendritic cells induced by a natural ligand, the LAG-3 protein CD223)", Blood, Sep. 15, 2003, 102 (6), 2130-7.

(Continued)

*Primary Examiner* — Gerald R Ewoldt
(74) *Attorney, Agent, or Firm* — Banner & Witcoff, Ltd

(57) ABSTRACT

Regulatory T cells (Treg) limit autoimmunity but can also attenuate the magnitude of anti-pathogen and anti-tumor immunity. Understanding the mechanism of Treg function and therapeutic manipulation of Treg in vivo requires identification of Treg selective receptors. A comparative analysis of gene expression arrays from antigen specific CD4+ T cells differentiating to either an effector/memory or a regulatory phenotype revealed Treg selective expression of LAG-3 (CD223), a CD4-related molecule that binds MHC class II. LAG-3 expression on CD4+ T cells correlates with the cells' in vitro suppressor activity, and ectopic expression of LAG-3 on CD4 T cells confers suppressor activity on the T cells. Antibodies to LAG-3 inhibit suppression both in vitro and in vivo. LAG-3 marks regulatory T cell populations and contributes to their suppressor activity.

6 Claims, 8 Drawing Sheets

(56) References Cited

OTHER PUBLICATIONS

Triebel: "LAG-3: a regulator of T-cell and DC responses and its use in therapeutic vaccination", Trends in Immunology, vol. 24, No. 12, Dec. 2003, pp. 619-622.

Subramanyam et al.: "Soluble human lymphocyte activation gene-3 modulates allospecific T cell responses", Int. Immunol., 1998, vol. 10, No. 4; pp. 679-689.

Workman et al.: "Phenotype analysis of the murine CD-4 related glycoprotein, CD223 (LAG-3)", Eur. J. Immunol, 2002, vol. 32, pp. 2255-2263.

Workman et al.: "Cutting Edge: Molecular analysis of the Negative Regulatory Function of the Lymphocyte Activation Gene-3", J. Immunol, 2002, vol. 169, pp. 5392-5395.

Huard et al., "T Cell Major Histocompatibility Complex Class II Molecules Down-Regulate CD4+ T Cell Clone Responses Following LAG-3 Binding," European Journal of Immunology, May 1, 1996; vol. 26, No. 5, pp. 1180-1186.

Prigent et al., "Lymphocyte activation gene-3 induces tumor regression and antitumor immune responses," Eur. J. Immunol. 29: 3867-3876, 1999.

"Notice of Reasons for Rejection," as dispatched by the Japanese Patent Office on Jan. 28, 2013 in Japanese Patent Application No, 2010-253326 and Engiish translation thereof, especially pp. 1-4 of English translation.

WO9858059 (A1) Abstract/Bibliographic data, Dec. 23, 1998, 2 pages, downloaded from http://worldwide.espacenet.com/publicationDetails.

WO9703695 (A1), Abstract/Bibliographic data, Feb. 6, 1997, 2 pages, downloaded from http://woridwide.espacenet.com/publicationDetails.

ANTI-CANCER VACCINE COMPOSITION COMPRISING AN ANTI-CD223 ANTIBODY AND KIT COMPRISING AN ANTI-CANCER VACCINE AND AN ANTI-CD223 ANTIBODY

The United States government, National Institutes of Health, provided funding (AI39480) for work that underlies the invention. Under the terms of that funding agreement, the United States government retains certain rights in the invention.

FIELD OF THE INVENTION

The invention relates to therapeutic and drug screening methods.

BACKGROUND OF THE INVENTION

A variety of diseases are characterized by the development of progressive immunosuppression in a patient. The presence of an impaired immune response in patients with malignancies has been particularly well documented. Cancer patients and tumor-bearing mice have been shown to have a variety of altered immune functions such as a decrease in delayed type hypersensitivity, a decrease in lytic function and proliferative response of lymphocytes. S. Broder et al., N. Engl. J. Ned., 299: 1281 (1978); E. M. Hersh et al., N. Engl. J. Med., 273: 1006 (1965); North and Burnauker, (1984). Many other diseases or interventions are also characterized by the development of an impaired immune response. For example, progressive immunosuppression has been observed in patients with acquired immunodeficiency syndrome (AIDS), sepsis, leprosy, cytomegalovirus infections, malaria, and the like, as well as with chemotherapy and radiotherapy. The mechanisms responsible for the down-regulation of the immune response, however, remain to be fully elucidated.

The immune response is a complex phenomenon. T lymphocytes (T cells) are critical in the development of all cell-mediated immune reactions. Helper T cells control and modulate the development of immune responses. Cytotoxic T cells (killer T cells) are effector cells which play an important role in immune reactions against intracellular parasites and viruses by means of lysing infected target cells. Cytotoxic T cells have also been implicated in protecting the body from developing cancers through an immune surveillance mechanism. Regulatory T cells block the induction and/or activity of T helper cells. T cells do not generally recognize free antigen, but recognize it on the surface of other cells. These other cells may be specialized antigen-presenting cells capable of stimulating T cell division or may be virally-infected cells within the body that become a target for cytotoxic T cells.

Cytotoxic T cells usually recognize antigen in association with class I Major Histocompatibility Complex (MHC) products which are expressed on all nucleated cells. Helper T cells, and most T cells which proliferate in response to antigen in vitro, recognize antigen in association with class II MHC products. Class II products are expressed mostly on antigen-presenting cells and on some lymphocytes. T cells can be also divided into two major subpopulations on the basis of their cell membrane glycoproteins as defined with monoclonal antibodies. The CD4+ subset which expresses a 62 kD glycoprotein usually recognizes antigen in the context of class II antigens, whereas the CD8+ subset expresses a 76 Kd glycoprotein and is restricted to recognizing antigen in the context of Class I MHC.

Augmentation of the immune response in immune compromised animals via infusions of lymphokines, adoptive immunotherapy has met with variable and limited success. Methods are needed to improve this type of treatment. For example, lymphocyte, blood and other cell infusions are provided to immunodeficient patients in certain settings. However, accelerating and enhancing the reconstitution of a healthy T cell population could provide significant increased benefit and efficacy to such patients.

A number of conditions can result in deleterious T cell activity. For example, T cell mediated autoimmune and inflammatory diseases are characterized by deleterious T cell activity in which T cells which recognize self antigens proliferate and attack cells which express such antigens. Other examples include the occurrence of graft rejection mediated by host T cells and graft vs. host disease.

Existing immunosuppressive therapies available to treat these conditions include administration of immunosuppressive compounds such as cyclosporine A, FK506 and rapamycin. However, these therapies are not completely effective and are associated with significant adverse side effects such as nephrotoxicity, hepatotoxicity, hypertension, hirsutism, and neurotoxicity. Thus additional therapies which can more effectively suppress T cell activity with fewer side effects are needed to treat these conditions.

Lymphocyte homeostasis is a central biological process that is tightly regulated. Tanchot, C. et al., Semin. Immunol. 9: 331-337 (1997); Marrack, P. et al., Nat. Immunol. 1: 107-111 (2000); C. D. Surh, C. D. and Sprent, J., Microbes. Infect. 4: 51-56 (2002); Jameson, S. C., Nat. Rev. Immunol. 2: 547-556 (2002). While the molecular control of this process is poorly understood, molecules involved in mediating two signaling pathways are thought to be essential. First, recognition of self major histocompatibility (MHC) molecules is important in maintaining naïve T cell homeostasis and memory T cell function. Takeda, S. et al., Immunity 5: 217-228 (1996); Tanchot, C. et al., Science 276:2057-2062 (1997).

Furthermore, recent studies have demonstrated that T cell receptor (TCR) expression is required for the continued survival of naïve T cell. Polic, B. et al., Proc. Natl. Acad. Sci. 98: 8744-8749 (2001); Labrecque, N. et al., Immunity 15: 71-82 (2001). Second, cytokines that signal via the common gamma (γc) chain are critical for naïve T cell survival and homeostasis, particularly interleukin-7 (IL-7). Schluns, K. S. et al., Nat. Immunol. 1: 426-432 (2000); Tan, J. T. et al., Proc. Natl. Acad. Sci. 98: 8732-8737 (2001). All of these molecules positively regulate T cell homeostasis. In contrast, only CTLA-4 and TGF-β have been implicated in negatively regulating T cell homeostasis, although this has jet to be confirmed by T cell transfer into lymphopenic hosts or analysis of neonatal expansion. Waterhouse, P. et al., Science 270: 985-988 (1995); Tivol, E. A. et al., Immunity 3: 541-547 (1995); Lucas, P. J. et al., J. Exp. Med. 191: 1187-1196 (2000); Gorelik, L. and Flavell, R. A., Immunity 12: 171-181 (2000).

LAG-3 is particularly interesting due to its close relationship with CD4. LAG-3 has a similar genomic organization to CD4 and resides at the same chromosomal location. Bruniquel, D. et al., Immunogenetics 47: 96-98 (1997). LAG-3 is expressed on activated CD4+ and CD8+ αβ T lymphocytes and a subset of γδ T cells and NK cells. Baixeras, E. et al., J. Exp. Med. 176: 327-337 (1992); Triebel, F. et al., J. Exp. Med. 171: 1393-1405 (1990); Huard, B. et al., Immunogenetics 39: 213-217 (1994); Workman, C. J. et al., Eur. J. Immunol. 32: 2255-2263 (2002). Like CD4, LAG-3 binds to MHC class II molecules but with a much higher affinity. Huard, B. et al., Immunogenetics 39: 213-217 (1994); Huard, B. et al., Eur. J. Immunol. 25: 2718-2721 (1995).

BRIEF SUMMARY OF THE INVENTION

In a first embodiment of the invention a method is provided for treating a patient suffering from an autoimmune disease.

Autoimmune T cells isolated from the patient are transfected in vitro with an expression construct comprising a coding sequence for CD223. The transfected Autoimmune T cells are then reinfused to the patient.

In a second embodiment of the invention a composition is provided. The composition comprises antibodies which specifically bind to CD223 and an anti-cancer vaccine.

In another embodiment of the invention a kit is provided. The kit comprises antibodies which specifically bind to CD223 and an anti-cancer vaccine.

In a fourth embodiment of the invention an improved method is provided for treating a cancer patient with an anti-cancer vaccine. An antibody which specifically binds to CD223 is administered to the cancer patient. An anti-cancer vaccine is also administered. The antibody increases magnitude of anti-cancer response of the cancer patient to the anti-cancer vaccine.

A fifth embodiment of the invention provides a method to overcome suppression of an immune response to an anti-cancer vaccine. An antibody which specifically binds to CD223 is administered to a cancer patient with regulatory T cells which suppress an immune response to an anti-cancer vaccine. An anti-cancer vaccine is also administered to the patient. The antibody increases the response of the cancer patient to the anti-cancer vaccine.

In another embodiment of the invention a method is provided for increasing number of T cells in a mammal. An inhibitory agent which binds to CD223 protein or CD223 mRNA is administered to the mammal. The inhibitory agent inhibits activity or expression of CD223.

In yet another embodiment of the invention a method is provided for decreasing number of T cells in a mammal. An expression construct which encodes CD223 is administered to the mammal. CD223 is expressed from the expression construct and concentration of CD223 in the mammal is increased. The number of T cells in the mammal is decreased.

In still another embodiment of the invention a method is provided for decreasing number of T cells in a mammal. A population of CD223+ T cells is administered to the mammal. The concentration of CD223 in the mammal is increased and the number of T cells in the mammal is thereby decreased.

According to another aspect of the invention a polypeptide consisting of 50 or less contiguous amino acid residues of CD223 is provided. The polypeptide comprises an amino acid sequence KIEELE as shown in SEQ ID NO: 5.

Another aspect of the invention is a fusion polypeptide which comprises at least two segments. A first segment consists of 50 or less contiguous amino acid residues of CD223. The first segment comprises an amino acid sequence KIELLE as shown in SEQ ID NO: 5. The second segment comprises an amino acid sequence which is not found in CD223 as shown in SEQ ID NO: 2 or 4.

In an additional embodiment a method is provided for testing substances for potential activity as a drug for treating cancer, autoimmune disease, chronic infections, AIDS, or bone marrow transplantation recipients. A test substance is contacted with a CD223 protein or CD223 protein fragment comprising an amino acid sequence KIELLE as shown in SEQ ID NO: 5. Then one determines whether the test substance bound to the CD223 protein or CD223 protein fragment. The test substance is identified as a potential drug for treating cancer, autoimmune disease, chronic infections, AIDS, or bone marrow transplantation recipients if the test substance bound to the CD223 protein or CD223 protein fragment.

Another embodiment provided by the present invention is a method for testing substances for potential activity as a drug for treating cancer, chronic infections, AIDS, or bone marrow transplantation recipients. A test substance is contacted with a CD223 protein. CD223 activity is determined in the presence and absence of the test substance. A test substance is identified as a potential drug for treating cancer, chronic infections, AIDS, or bone marrow transplantation recipients if the test substance inhibits the CD223 activity.

According to another aspect of the invention a method is provided for testing substances for potential activity as a drug for treating autoimmune disease. A test substance is contacted with a CD223 protein. CD223 activity is determined in the presence and absence of the test substance. A test substance is identified as a potential drug for treating autoimmune disease if the test substance increases the CD223 activity.

Another embodiment of the invention is a method of testing substances for potential activity as a drug for treating cancer, chronic infections, AIDS, or bone marrow transplantation recipients. A CD223+ T cell is contacted with a test substance. CD223 expression is determined in the cell in the presence and absence of the test substance. A test substance is identified as a potential drug for treating cancer, chronic infections, AIDS, or bone marrow transplantation recipients if the test substance inhibits the CD223 expression in the T cell.

Yet another aspect of the invention is another method of testing substances for potential activity as a drug for treating autoimmune disease. A test substance is contacted with a CD223+ T cell. CD223 expression in the cell is determined in the presence and absence of the test substance. A test substance is identified as a potential drug for treating autoimmune disease if the test substance increases the CD223 expression in the T cell.

Still another aspect of the invention is a method of isolating CD223+ T cells or CD223− T cells. A mixed population of T cells is contacted with an antibody which specifically binds to CD223 according to SEQ ID NO: 2 or 4. T cells which are bound to the antibody are separated from T cells which are not bound to the antibody. A population of CD223+ T cells and a population of CD223− T cells are thereby formed.

Another embodiment of the invention is an isolated soluble murine CD223 protein comprising residues 1 to 431 and lacking residues 467 to 521.

Still another aspect of the invention is an isolated soluble human CD223 protein comprising residues 1 to 440 and lacking residues 475 to 525.

Yet another aspect of the invention is a method for decreasing number of T cells in a mammal. A soluble CD223 protein is administered to the mammal. MHC class II-restricted/CD4+ T cell responses in the mammal are thereby modulated.

BRIEF DESCRIPTION OF THE DRAWINGS

(FIG. 1A) C3-HAhigh transgenic mice express high levels of HA in various epithelial compartments, with the highest level expressed in pulmonary epithelia. C3-HAhigh recipients die 4-7 days after adoptive transfer of 2.5×106 HA-specific TCR transgenic (6.5) CD4+ T cells due to pneumonitis associated with a transient effector phase of activation occurring prior to development of an anergic phenotype. Transfer of smaller numbers of 6.5 CD4+ T cells results in less severe pulmonary pathology and the C3-HAhigh recipients survive the transfer. Residual 6.5 T cells become anergic as defined by their inability to produce γ-interferon or proliferate to HA antigen in vitro. Mice receiving a sublethal dose of 6.5 T cells are protected from subsequent infusion of 2.5×10⁶ naive 6.5 T cells. Thus, the initial tolerized T cells develop Treg activity that suppresses lethal pneumonitis induced by the second high dose of 6.5 T cells. (FIG. 1B) Localization of effector/memory vs. suppressed T cells in C3-HAhigh mice. Naive 6.5 T cells (Thy 1.1+/1.2−) were adoptively transferred into C3-HAhigh recipients (Thy 1.1−/1.2+), either in the absence or in the presence of 6.5 anergic/Treg cells (Thy 1.1−/1.2+). Spleens and lungs were harvested 3 days after adoptive transfer and Thy 1.1+ cells were stained by immunohistochemistry. In the absence of Treg cells, T effector cells are scattered in the splenic follicles (FIG. 1B(a)) and infiltrate the pulmonary vessels (FIG. 1B(b)). In the presence of Treg cells, suppressed HA-specific 6.5 T cells become sequestered in the splenic peri-arteriolar lymphatic sheath (FIG. 1B(c)) and fail to infiltrate the pulmonary vessels (FIG. 1B(d)).

(FIG. 2B) Cell surface LAG-3 protein levels were assessed by antibody staining Splenocytes were harvested from C3-HAhigh, wild type B10.D2 mice immunized with Vac-HA, or wt B10.D2 mice 5 days after i.v. injection with 6.5+/−Thy1.1+/− splenocytes, and prepared into a single cell suspension. All samples were first incubated with whole rat IgG to block Fc receptors. Cells were stained with TCR specific anti-6.5-biotin+SA-APC, LAG-3-PE, or the corresponding isotype controls. Cells were double gated on the total lymphocyte population and 6.5 positive lymphocytes. Isotype control-dashed line, Naïve cells—light gray line, Effector/memory cells—dark gray line, Anergic/Treg cells—black line. (FIG. 2C) Analysis of multiple samples of anergic/Treg populations over many experiments confirms a direct correlation between LAG-3 level and IL-10 mRNA level.

(FIG. 3A) Anergic/Treg 6.5 CD4+ T cells from C3-HAhigh recipient spleens 5 days after transfer were stained for LAG-3 and CD25 expression, compared to isotype controls. (FIG. 3B) Cells were sorted into 4 populations based on their surface LAG-3 and CD25 staining: LAG-3highCD25high, LAG-3highCD25low, LAG-3lowCD25high, and LAG-3lowCD25low. 1×10⁵ of each of the different sorted subsets of cells were added as suppressors in an in vitro suppression assay with 1×10⁴ naive 6.5 CD4+ as responders. LAG-3lowCD25low cells were least suppressive. LAG-3highCD25high, LAG-3highCD25low, and LAG-3lowCD25high are comparable in suppressive activity, with LAG-3highCD25high double positive cells exhibiting the most suppressive activity. This is the representative result of three reproducible experiments.

(FIG. 5A) C3-HAhigh mice pretreated with 8,000 6.5 CD4+ T cells survived subsequent challenge with 2.5× 106 6.5 CD4+ T cells given 4 days after the initial transfer establishment of Treg population (w/ Protection). Without the sublethal pretreatment, the C3-HAhigh recipients died 4-6 Days after lethal challenge (No Protection). Monoclonal anti-LAG-3 antibody (200 μg) was given i.v. to the C3-HAhigh mice with the lethal dose of 6.5 T cells 4 days after they were pretreated with 8,000 6.5 CD4+ T cells and another dose of 200 μg was given 2 days later. Anti-LAG-3 antibody treated mice could no longer tolerate the subsequent lethal challenge (Protection+aLAG-3). In contrast, treatment with isotype control antibody rat IgG1 could not eliminate the in vivo suppression (Protection+RatIgG1). (FIGS. 5B and 5C) Anti-LAG-3 mAb does not hyper-activate naive 6.5 CD4+ T cells in the absence of Treg. C3-HAhigh mice received either 2.5× 105 (sublethal dose; FIG. 5B) or 8×105 (partial lethality between 7 and 14 days after transfer; FIG. 5C) naïve 6.5 CD4+ T cells in combination with anti-LAG-3 antibody, control rat IgG1, or no antibody. No lethality was observed with the anti-LAG-3 antibody infusions at the 2.5×105 dose whereas lethality at 8×105 dose was not affected by anti-LAG-3 antibody.

(FIG. 6A) Natural CD4+CD25+ T cells have higher levels of LAG-3 mRNA expression compared to their CD4+CD25− counterpart. CD4+CD25+ and CD4+CD25− T cells were purified from wild type BALB/c lymph nodes. CD4+CD25+ T cells, the population documented to contain natural regulatory T cells, have significantly higher mRNA levels for CD25 and LAG-3, as well as for CTLA-4, GITR and Foxp3, as compared to their CD4+CD25− counterpart (Expression of each mRNA in the CD4+CD25− subset was normalized to a value of 1). (FIG. 6B) LAG-3 surface staining is negative on CD4+CD25+ natural regulatory T cells, as in their CD4+CD25− counterpart. However, intracellular staining for LAG-3 reveals a positive population in CD4+CD25+, but not in CD4+CD25− T cells. (FIG. 6C) Sorted CD4+CD25+ T cells from BALB/c mouse lymph nodes were used as suppressors and CD4+CD25− T cells as responders in an in vitro suppression assay (suppressor:effector ratio of 0.04:1), with anti-CD3 antibodies (0.5 μg/ml) as the T cell stimulus. Anti-LAG-3 antibodies at the concentration of 50 μg/ml reverse the in vitro suppression of natural CD4+CD25+ regulatory T cells whereas isotype control antibody does not. (FIG. 6D) After the suppressor assay in C, the CD4+CD25+ cells (distinguished from the effector cells by Thy1.2 marking) were stained with anti-LAG-3 or isotype control antibody.

Figure 1A:
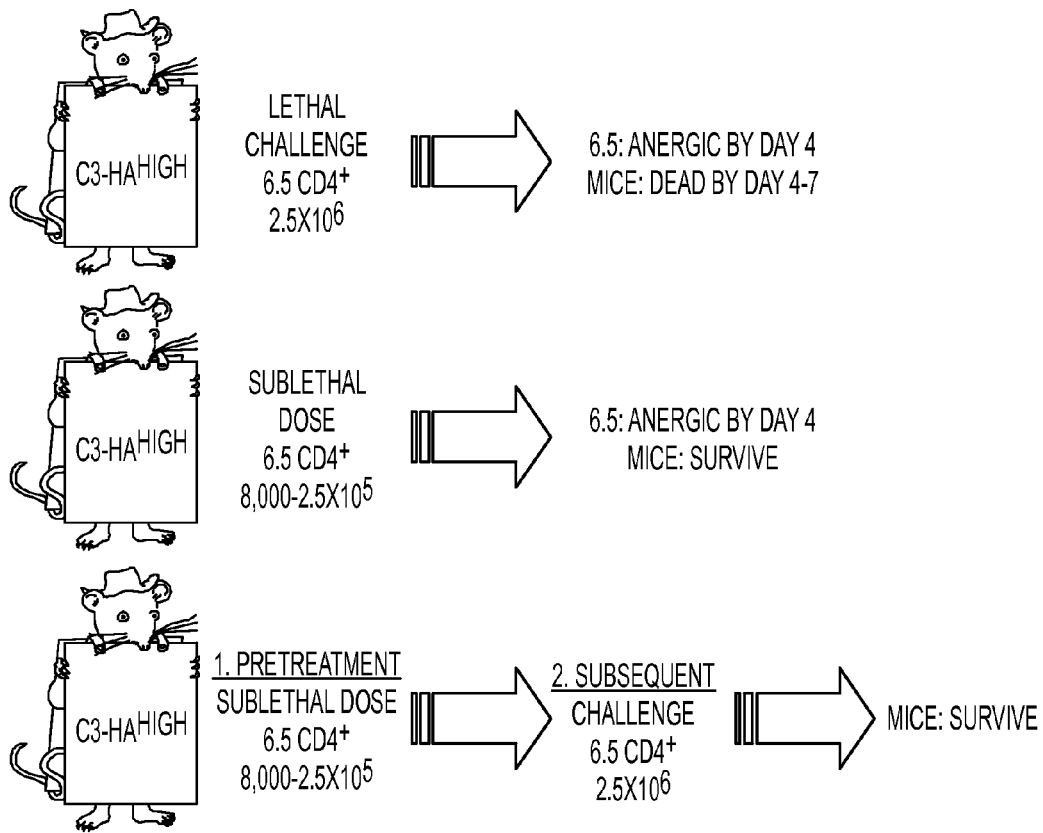
FIG. 1A to 1B. HA specific CD4+ T cells become tolerant and develop regulatory T cell activity upon adoptive transfer into C3-HAhigh transgenic mice.

or in combination with Phogrin T cell clone 4 (obtained from John Hutton) cells transduced with vector (MIG), LAG-3, or a signaling-defective mutant, LAG-3 K, into NOD/SCID mice. NOD/SCID mice (5/group) were monitored for diabetes.

DETAILED DESCRIPTION OF THE INVENTION

LAG-3 is a CD4-related, activation-induced cell surface molecule that binds to MHC class II with high affinity. We have found that aged LAG-3 deficient mice have twice as many $CD4^+$ and $CD8^+$ T cells than wild type controls. LAG-3 deficient T cells show enhanced homeostatic expansion in lymphopenic hosts, which is dependent on LAG-3 ligation of MHC class II molecules. This was abrogated by ectopic expression of wild type LAG-3 but not by a signaling defective mutant. This deregulation of T cell homeostasis results in the expansion of multiple cell types. Our data suggest that LAG-3 negatively regulates $CD4^+$ and $CD8^+$ T cell homeostasis, and present LAG-3 as a therapeutic target for accelerating T cell engraftment following bone marrow transplantation.

CD223, also known as lymphocyte antigen gene-3 or LAG-3, is a CD4-related activation-induced cell surface protein that binds to MHC class II molecules with high affinity. Baixeras, E. et al., *J. Exp. Med.* 176: 327 (1992). See Triebel, F., "Lag-3(CD223)", *Protein Reviews on the Web (PROW)* 3:15-18 (2002) at the URL address: http file type, www host server, domain name ncbi.nlm.gov, directory PROW, subdirectory guide, document name 165481751_g.htm.; Triebel, F. et al., "LAG-3, a novel lymphocyte activation gene closely related to CD4", *J. Exp. Med.* 171: 1393-1405 (1990). A representative murine DNA and amino acid sequence for CD223 is set forth as SEQ ID NOS: 1 and 2, respectively. See also GenBank Accession Code X9113. A representative human DNA and amino acid sequence for CD223 is set forth as SEQ ID NOS: 3 and 4, respectively. See also GenBank Accession Number X51985. These sequences are derived from single individuals. It is expected that allelic variants exist in the population which differ at less than about 5% of the positions. Such allelic variants are included within the meaning of CD223 of murine or human origin.

Regulatory T cells are a subgroup of T cells that function by inhibiting effector T cells. Regulatory T cells are $CD223^+$ and are typically also $CD4^+CD25^+$. Regulatory T cells play a central role in balancing autoimmune tolerance and immune responsiveness. Such cells can be isolated from CD223− cells using antibodies and separation techniques known in the art. These include but are not limited to immunoaffinity chromatography, FACS, immunoprecipitation, etc. The $CD223^+$ cells can be administered to autoimmune disease, allergy, or asthma patients. In the case of an autoimmune disease patient the cells can be pre-activated with autoantigen. $CD223^-$ cells can be similarly transferred to cancer patients, bacterial or vial infection patients, or AIDS patients.

A comparative analysis of gene expression arrays from antigen specific CD4+ T cells differentiating to either an effector/memory or a regulatory phenotype revealed Treg-specific expression of LAG-3, a CD4 homologue that binds MHC class II. LAG-3high CD4+ T cells display in vitro suppressor activity and antibodies to LAG-3 inhibit the suppression both in vitro and in vivo. These findings identify LAG-3 as a Treg specific receptor or co-receptor modulating suppressor activity. Manipulation of Treg cells via LAG-3 can therefore be used to enhance immunotherapy of autoimmune diseases, cancer and infectious diseases as well as enhance lymphocyte engraftment in settings of donor lymphocyte infusion, bone marrow transplantation and adoptive T cell transfer.

CD223 is a regulatory T cell specific cell surface molecule that regulates the function of regulatory T cells. The function of a regulatory T cell may be enhanced by enhancing or increasing CD223 activity, or by increasing the number of CD223+ cells in a T cell population. Enhancing the function of regulatory T cells in an organism may be used to limit the immune T cell response in those circumstances where such a response is undesirable, such as when a subject suffers from autoimmune disease. Conversely, the function of a regulatory T cell may be inhibited by inhibiting CD223 activity or by decreasing the number of CD223+ cells in a T cell population. Inhibiting the function of regulatory T cells in an organism may be used to enhance the immune T cell response in those circumstances where such a response is desirable, such as in a patient suffering from cancer, chronic infection, or a bone marrow transplant recipient.

When treating a cancer patient with an inhibitory agent that binds to CD223 protein or mRNA, one may optionally co-administer an anti-tumor vaccine. Such vaccines may be directed to isolated antigens or to groups of antigens or to whole tumor cells. It may be desirable to administer the inhibitory agent with chemotherapeutic agents. Treatment with multiple agents need not be done using a mixture of agents but may be done using separate pharmaceutical preparations. The preparations need not be delivered at the same exact time, but may be coordinated to be delivered to a patient during the same period of treatment, i.e., within a week or a month or each other. Thus a composition comprising two active ingredients may be constituted in the body of the patient. Any suitable anti-tumor treatment can be coordinated with the treatments of the present invention targeted to CD223. Similarly, if treating patients with infections, other anti-infection agents can be coordinated with the treatment of the present invention targeted to CD223. Such agents may be small molecule drugs, vaccines, antibodies, etc.

The number of $CD223^+$ cells in a T cell population can be modified by using an antibody or other agent that selectively binds to CD223. $CD223^+$ cells represent an enriched population of regulatory T-cells that can be introduced back into the original source of the T cells or into another compatible host to enhance regulatory T cell function. Alternatively, the $CD223^-$ cells represent a population of T cells deficient in regulatory T cell activity that can be reintroduced into the original source of the T cells or another compatible host to inhibit or reduce regulatory T cell function while retaining general T cell activity.

Any desired means for either increasing or decreasing (modulating) CD223 activity can be used in the methods of the invention. This includes directly modulating the function of CD223 protein, modulating CD223 signal transduction, and modulating expression of CD223 in T cells by modulating either transcription or translation or both. Those means which selectively modulate CD223 activity are preferred over nonselective modulators. Also, those inhibitory means which create a transient CD223 deficiency in a population of T cells which then return to normal levels of CD223 activity may be preferred for treating a temporary T cell deficiency. The transiently deficient T cells may be used to reconstitute a diminished T cell population with T cells that will be genetically normal with respect to CD223. Such a temporary T cell deficiency occurs, for example, in patients receiving a stem cell transfer following myoablation. Modulation of CD223 activity can be performed on cells in vitro or in whole animals, in vivo. Cells which are treated in vitro can be administered to a patient, either the original source of the cells or au unrelated individual.

To inhibit the function of CD223, CD223 antibodies or small molecule inhibitors can be used. Antibodies or antibody fragments that are useful for this purpose will be those that can bind to CD223 and block its ability to function. Such antibodies may be polyclonal antibodies, monoclonal antibodies (see, e.g. Workman, C. J. et al., "Phenotypic analysis of the murine CD4-related glycoprotein, CD223 (LAG-3)", *Eur. J. Immunol.* 32:2255-2263 (2002)), chimeric antibodies, humanized antibodies, single-chain antibodies, soluble MHC class II molecules, antibody fragments, etc.

Antibodies generated against CD223 polypeptides can be obtained by direct injection of the CD223 polypeptides into an animal or by administering CD223 polypeptides to an animal, preferably a nonhuman. The antibody so obtained will then bind the CD223 polypeptides itself. In this manner, even a sequence encoding only a fragment of the CD223 polypeptide can be used to generate antibodies binding the whole native CD223 polypeptide.

For preparation of monoclonal antibodies, any technique which provides antibodies produced by continuous cell line cultures can be used. Examples include the hybridoma technique (Kohler and Milstein, 1975, Nature, 256:495-497), the trioma technique, the human B-cell hybridoma technique (Kozbor et al., 1983, Immunology Today 4:72), and the EBV-hybridoma technique to produce human monoclonal antibodies (Cole, et al., 1985, in Monoclonal Antibodies and Cancer Therapy, Alan R. Liss, Inc., pp. 77-96).

Techniques described for the production of single chain antibodies (U.S. Pat. No. 4,946,778) can be readily used to produce single chain antibodies to CD223 polypeptides. Also, transgenic mice may be used to express humanized antibodies to immunogenic CD223 polypeptides.

To enhance or activate the function of CD223, any agent which increases the level of CD223 or the activity of existing CD223 in the T cell may be used. Such agents may be identified using the screening assays described below. Expression vectors encoding CD223 can also be administered to increase the gene dosage. The expression vectors can be plasmid vectors or viral vectors, as are known in the art. Any vector can be chosen by the practitioner for particularly desirable properties.

Autoimmune disease which are amenable to treatments according to the present invention include autoimmune hemolytic anemia, autoimmune thrombocytopenia purpura, Goodpasture's syndrome, pemphigus vulgaris, acute rheumatic fever, mixed essential cryoglobulinemia, systemic lupus erythematosus, insulin-dependent diabetes mellitus, rheumatoid arthritis, Graves' disease, Hashimoto's thyroiditis, myasthenia gravis, and multiple sclerosis. Autoimmune T cells can be isolated from autoimmune disease patients as is known in the art. These can be transfected with a coding sequence for CD223. Any desirable expression vector can be used for expressing CD223. These include without limitations plasmids and viral vectors. The expression regulatory signals can be derived from CD223 itself or from other genes. After transfection with CD223 expression construct the T cells can be reintroduced to the patient. Methods for infusing blood cells to a patient are well known in the art.

Compositions comprising a mixture of antibodies which specifically bind to CD223; and an anti-cancer vaccine can be made in vitro. Preferably the composition is made under conditions which render it suitable for use as a pharmaceutical composition. Pharmaceutical compositions may be sterile and pyrogen-free. The components of the composition can also be administered separately to a patient within a period of time such that they are both within the patient's body at the same time. Such a time-separated administration leads to formation of the mixture of antibodies and vaccine within the patient's body. If the antibody and vaccine are to be administered in a time-separated fashion, they may be supplied together in a kit. Within the kit the components may be separately packaged or contained. Other components such as excipients, carriers, other immune modulators or adjuvants, instructions for administration of the antibody and the vaccine, and injection devices can be supplied in the kit as well. Instructions can be in a written, video, or audio form, can be contained on paper, an electronic medium, or even as a reference to another source, such as a website or reference manual.

Anti-CD223 antibodies of the invention can be used to increase the magnitude of anti-cancer response of the cancer patient to the anti-cancer vaccine. It can also be used to increase the number of responders in a population of cancer patients. Thus the antibodies can be used to overcome immune suppression found in patients refractory to anti-cancer vaccines. The anti-cancer vaccines can be any that are known in the art, including, but not limited to whole tumor cell vaccines, isolated tumor antigens or polypeptides comprising one or more epitopes of tumor antigens.

Expression of CD223 in T cells can be modulated at the transcriptional or translational level. Agents which are capable of such modulation can be identified using the screening assays described below.

Translation of CD223 mRNA can be inhibited by using ribozymes, antisense molecules, small interference RNA (siRNA; See Elbashir, S. M. et al., "Duplexes of 21-nucleotide RNAs mediate RNA interference in cultured mammalian cells", *Nature* 411:494-498 (2001)) or small molecule inhibitors of this process which target CD223 mRNA. Antisense technology can be used to control gene expression through triple-helix formation or antisense DNA or RNA, both of which methods are based on binding of a polynucleotide to DNA or RNA. For example, the 5' coding portion of the polynucleotide sequence, which codes for the mature polypeptides of the present invention, is used to design an antisense RNA oligonucleotide of from about 10 to 40 base pairs in length. A DNA oligonucleotide is designed to be complementary to a region of the gene involved in transcription (triple helix—see Lee et al., Nucl. Acids Res., 6:3073 (1979); Cooney et al, Science, 241:456 (1988); and Dervan et al., Science, 251: 1360 (1991)), thereby preventing transcription and the production of CD223. The antisense RNA oligonucleotide hybridizes to the mRNA in vivo and blocks translation of the mRNA molecule into the CD223 polypeptide (Antisense—Okano, J. Neurochem., 56:560 (1991); Oligodeoxynucleotides as Antisense Inhibitors of Gene Expression, CRC Press, Boca Raton, Fla. (1988)). The oligonucleotides described above can also be delivered to cells by antisense expression constructs such that the antisense RNA or DNA may be expressed in vivo to inhibit production of CD223. Such constructs are well known in the art.

Antisense constructs, antisense oligonucleotides, RNA interference constructs or siRNA duplex RNA molecules can be used to interfere with expression of CD223. Typically at least 15, 17, 19, or 21 nucleotides of the complement of CD223 mRNA sequence are sufficient for an antisense molecule. Typically at least 19, 21, 22, or 23 nucleotides of CD223 are sufficient for an RNA interference molecule. Preferably an RNA interference molecule will have a 2 nucleotide 3' overhang. If the RNA interference molecule is expressed in a cell from a construct, for example from a hairpin molecule or from an inverted repeat of the desired CD223 sequence, then the endogenous cellular machinery will create the overhangs. siRNA molecules can be prepared by chemical synthesis, in vitro transcription, or digestion of long dsRNA by Rnase III or Dicer. These can be introduced into cells by transfection, electroporation, or other methods known in the art. See Hannon, G J, 2002, RNA Interference, *Nature* 418: 244-251; Bernstein E et al., 2002, The rest is silence. *RNA* 7: 1509-1521; Hutvagner G et al., RNAi: Nature abhors a double-strand. *Curr. Opin. Genetics & Development* 12: 225-232; Brummelkamp, 2002, A system for stable expression of short interfering RNAs in mammalian cells. *Science* 296: 550-553; Lee N S, Dohjima T, Bauer G, Li H, Li M-J, Ehsani A, Salvaterra P, and Rossi J. (2002). Expression of small interfering RNAs targeted against HIV-1 rev transcripts in human cells. *Nature Biotechnol.* 20:500-505; Miyagishi M, and Taira K. (2002). U6-promoter-driven siRNAs with four uridine 3' overhangs efficiently suppress targeted gene expression in mammalian cells. *Nature Biotechnol.* 20:497-500; Paddison P J, Caudy A A, Bernstein E, Hannon G J, and Conklin D S. (2002). Short hairpin RNAs (shRNAs) induce sequence-specific silencing in mammalian cells. *Genes & Dev.* 16:948-958; Paul C P, Good P D, Winer I, and Engelke D R. (2002). Effective expression of small interfering RNA in human cells. *Nature Biotechnol.* 20:505-508; Sui G, Soohoo C, Affar E-B, Gay F, Shi Y, Forrester W C, and Shi Y. (2002). A DNA vector-based RNAi technology to suppress gene expression in mammalian cells. *Proc. Natl. Acad. Sci. USA* 99(6):5515-5520; Yu J-Y, DeRuiter S L, and Turner D L. (2002). RNA interference by expression of short-interfering RNAs and hairpin RNAs in mammalian cells. *Proc. Natl. Acad. Sci. USA* 99(9):6047-6052.

In addition to known modulators, additional modulators of CD223 activity that are useful in the methods of the invention can be identified using two-hybrid screens, conventional biochemical approaches, and cell-based screening techniques, such as screening candidate molecules for an ability to bind to CD223 or screening for compounds which inhibit CD223 activity in cell culture. As one example, the inventors have identified a hen egg lysozyme (HEL), 48-62-specific, H-2A$^k$-restricted murine CD4$^+$ T cell hybridoma 3A9 that does not express CD223, even after activation. Ectopic expression of wild type, but not signaling defective, CD223 significantly reduced the IL-2 response of this T cell hybridoma to its specific peptide. This provides a simple in vitro assay system to screen for CD223 activity modulators. This latter method may identify agents that directly interact with and modulate CD223, as well as agents that indirectly modulate CD223 activity by affecting a step in the CD223 signal transduction pathway.

Cell-based assays employing cells which express CD223 can employ cells which are isolated from mammals and which naturally express CD223. Alternatively, cells which have been genetically engineered to express CD223 can be used. Preferably the genetically engineered cells are T cells.

Agents which modulate CD223 activity by modulating CD223 gene expression can be identified in cell based screening assays by measuring amounts of CD223 protein in the cells in the presence and absence of candidate agents. CD223 protein can be detected and measured, for example, by flow cytometry using anti-CD223 specific monoclonal antibodies. CD223 mRNA can also be detected and measured using techniques known in the art, including but not limited to Northern blot, RT-PCR, and array hybridization.

One particularly useful target sequence for identifying CD223 modulators is the amino acid motif KIEELE (SEQ ID NO: 5) in the CD223 cytoplasmic domain which is essential for CD223 function in vitro and in vivo. Screening assays for agents which bind this motif will identify candidate CD223 modulators whose activity as an inhibitor or activator of CD223 can be further characterized through further testing, such as in cell based assays. This motif can be contained within a polypeptide which consists of 50 or fewer contiguous amino acid residues of CD223. Alternatively, the motif can be contained within a fusion protein which comprises a portion of CD223 and all or a portion of a second (non-CD223) protein. The second protein may be a natural protein or can be a synthetic polypeptide, for example containing a histidine tag, or other useful polypeptide feature. Protein-protein binding assays are well known in the art and any of a variety of techniques and formats can be used.

CD223 can be post-translationally processed to yield a soluble form of the protein. The soluble form comprises at least amino acid residues 1 to 431 of murine CD223, and at least amino acid residues 1 to 440 of human CD223. The cytoplasmic tail is missing in each case. All or part of the transmembrane domain is missing as well. This soluble form modulates responses of MHC class II-restricted/CD4+ T cells. Thus the soluble form may be useful for administration to autoimmune disease patients, allergy patients, asthma patients, or cancer patients, for example. Administration of the soluble form may be by any of convenient means, including infusion, topical, or intravenous administration.

In accordance with the teachings of the invention, CD223 inhibitors may be administered to an organism to increase the number of T cells in the organism. This method may be useful for treating organisms suffering from conditions resulting in a low T cell population. Such conditions include diseases resulting from immunodeficiency such as AIDS, as well as disorders involving unwanted cellular invasion or growth, such as invasion of the body by foreign microorganisms (bacteria or viruses) or tumor growth or cancer.

Such a T cell deficiency is also an expected hazard for patients receiving a stem cell transfer following myoablation. The T cells of such patients are compromised and deliberately targeted for destruction so that they can be replaced with healthy donor T cells. The process of reconstituting a healthy T cell population from a stem cell transfer can take several months, during which time the patient is very susceptible to opportunistic infections which can be life threatening. By inhibiting CD223 in the donor T cells or using donor T cells that have been selected or engineered for a CD223 deficiency, T cell division is enhanced and the process of T cell reconstitution can be accelerated and the period of T cell deficiency can be reduced.

CD223 inhibitors may also be useful when administered in combination with conventional therapeutics to treat T cell proliferation sensitive disorders. For instance a tumor, which is a T cell proliferation sensitive disorder, is conventionally treated with a chemotherapeutic agent which functions by killing rapidly dividing cells. The CD223 inhibitors of the invention when administered in conjunction with a chemotherapeutic agent enhance the tumoricidal effect of the chemotherapeutic agent by stimulating T cell proliferation to enhance the immunological rejection of the tumor cells.

In accordance with the teachings of the invention, CD223 activators or expression enhancers may be administered to an organism to decrease the number of T cells in the organism and thereby decrease deleterious T cell activity. This method may be useful for treating organisms suffering from conditions resulting in an abnormally high T cell population or deleterious T cell activity, for example graft rejection mediated by host T cells, graft vs. host disease and T cell mediated autoimmune and inflammatory diseases such as rheumatoid arthritis, type 1 diabetes, muscular sclerosis, etc. The methods of the invention may be applied to any organism which contains T cells that express CD223. This includes, but is not limited to, any mammal and particularly includes humans and mice.

When methods of the invention are carried out in vivo, the effective amount of CD223 modulator used will vary with the particular modulator being used, the particular condition being treated, the age and physical condition of the subject being treated, the severity of the condition, the duration of the treatment, the nature of the concurrent therapy (if any), the specific route of administration and similar factors within the knowledge and expertise of the health practitioner. For example, an effective amount can depend upon the degree to which an individual has abnormally depressed levels of T cells.

When administered, the pharmaceutical preparations of the invention are applied in pharmaceutically-acceptable amounts and in pharmaceutically-acceptably compositions. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

CD223 modulators may be combined, optionally, with a pharmaceutically-acceptable carrier. The term "pharmaceutically-acceptable carrier" as used herein means one or more compatible solid or liquid filler, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt. The pharmaceutical compositions also may contain, optionally, suitable preservatives, such as: benzalkonium chloride; chlorobutanol; parabens and thimerosal.

Compositions suitable for parenteral administration conveniently comprise a sterile aqueous preparation of the anti-inflammatory agent, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

A variety of administration routes are available. The particular mode selected will depend, of course, upon the particular drug selected, the severity of the condition being treated and the dosage required for therapeutic efficacy. The methods of the invention, generally speaking, may be practiced using any mode of administration that is medically acceptable, meaning any mode that produces effective levels of the active compounds without causing clinically unacceptable adverse effects. Such modes of administration include oral, rectal, topical, nasal, interdermal, or parenteral routes. The term "parenteral" includes subcutaneous, intravenous, intramuscular, or infusion. Intravenous or intramuscular routes are not particularly suitable for long-term therapy and prophylaxis. They could, however, be preferred in emergency situations. Oral administration will be preferred because of the convenience to the patient as well as the dosing schedule.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active agent into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active agent. Other compositions include suspensions in aqueous liquids or non-aqueous liquids such as a syrup, elixir or an emulsion.

Other delivery systems can include time-release, delayed release or sustained release delivery systems. Such systems can avoid repeated administrations of the active agent, increasing convenience to the subject and the physician. Many types of release delivery systems are available and known to those of ordinary skill in the art. They include polymer base systems such as poly(lactide-glycolide), copolyoxalates, polycaprolactones, polyesteramides, polyorthoesters, polyhydroxybutyric acid, and polyanhydrides. Microcapsules of the foregoing polymers containing drugs are described in, for example, U.S. Pat. No. 5,075,109. Delivery systems also include non-polymer systems that are: lipids including sterols such as cholesterol, cholesterol esters and fatty acids or neutral fats such as mono-di- and tri-glycerides; hydrogel release systems; sylastic systems; peptide based systems; wax coatings; compressed tablets using conventional binders and excipients; partially fused implants; and the like. Specific examples include, but are not limited to: (a) erosional systems in which the anti-inflammatory agent is contained in a form within a matrix such as those described in U.S. Pat. Nos. 4,452,775, 4,667,014, 4,748,034 and 5,239,660 and (b) diffusional systems in which an active component permeates at a controlled rate from a polymer such as described in U.S. Pat. Nos. 3,832,253, and 3,854,480. In addition, pump-based hardware delivery systems can be used, some of which are adapted for implantation.

Use of a long-term sustained release implant may be particularly suitable for treatment of chronic conditions. Long-term release, are used herein, means that the implant is constructed and arranged to deliver therapeutic levels of the active ingredient for at least 30 days, and preferably 60 days. Long-term sustained release implants are well-known to those of ordinary skill in the art and include some of the release systems described above.

While the invention has been described with respect to specific examples including presently preferred modes of carrying out the invention, those skilled in the art will appreciate that there are numerous variations and permutations of the above described systems and techniques that fall within the spirit and scope of the invention as set forth in the appended claims.

EXAMPLES

Example 1

Negative Regulation of T Cell Homeostasis by LAG-3 (CD223)

The following example shows that LAG-3 (CD223) negatively regulates CD4+ and CD8+ T cell homeostasis, supporting its identification as a novel therapeutic target for accelerating T cell engraftment following bone marrow transplantation.

Wild type C57BL/6 mice have a constant number of $\alpha\beta^+$ T cells from 4 to 52 weeks of age. As previously reported, young 4 week old LAG-3$^{-/-}$ mice have normal T cell numbers. Miyazaki, T. et al., *Science* 272: 405-408 (1996). In contrast, the number of $\alpha\beta^+$ T cells in LAG-3$^{-/-}$ mice steadily increases from 3 months of age to numbers ~2-fold higher than wild type mice. This difference is highly significant given the tight homeostatic regulation of $\alpha\beta^+$ T cell number evidenced by the very low standard deviation. Both CD4+ and CD8+ cells were increased in LAG-3$^{-/-}$ mice but the CD4:CD8 ratio was unchanged. Similarly, LAG-3$^{-/-}$ mice transgenic for the OT-II TCR (ovalbumin 326-339-specific, H-2A$^b$-restricted) had an increased number CD4+ V$\alpha$2+ T cells compared with wild type control OT-II transgenic mice, except that these differences were evident at 5 weeks of age. Approximately 20% $\alpha\beta^+$ T cells and CD49b+ NK cells constitutively express LAG-3 in wild type mice (Workman, C. J. et al., *Eur. J. Immunol.* 32: 2255-2263 (2002)), and their numbers were also significantly increased in LAG-3$^{-/-}$ mice. Surprisingly, several other cell types such B220+ B cells, Gr-1+ granulocytes and Mac-1+ macrophages, none of which express LAG-3, were also increased in LAG-3$^{-/-}$ compared with control mice. The increased cell numbers observed in LAG-3$^{-/-}$ mice was consistent with a ~50% increase in the number of dividing BrdC cells in vivo. It is important to note that the differences in cell number observed between LAG-3$^{-/-}$ and wild type mice was highly consistent and reproducible. The absence of LAG-3 did not appear to have any significant effect on the cell surface phenotype of T cells from LAG-3$^{-/-}$ mice. These data support the idea that LAG-3 regulates the number of T cells in mice, and indirectly affects leukocyte numbers in general.

To determine if LAG-3 influences the homeostatic expansion of T cells in a lymphopenic environment, purified T cells were adoptively transferred into RAG$^{-/-}$ mice, which lack T and B cells, and T cell number in the spleen determined 15 days post-transfer. There was a 2.8-fold increase in the number of LAG-3$^{-/-}$ T cells compared with the wild type control. Remarkably, only a small percentage of the wild-type T cells expressed LAG-3 despite the clear effect that the absence of LAG-3 has on T cell expansion. This infers that brief, transient expression of LAG-3 may be sufficient for it to exert its effect on dividing cells. Increased expansion of CD4+ and CD8+ T cells was observed demonstrating that both cell types were equally affected by the absence of LAG-3. Interestingly, there was also a two-fold increase in the number of $\alpha\beta^-$ host-derived cells in recipients of LAG-3$^{-/-}$ versus LAG-3$^{+/+}$ T cells. This was consistent with the increased number of macrophages and granulocytes observed in unmanipulated LAG-3$^{-/-}$ mice. To ensure that the increased expansion of LAG-3$^{-/-}$ T cells observed in RAG$^{-/-}$ mice is independent of antigen specificity, we used purified T cells from OVA [Ovalbumin 257-264-specific, H-2K$^b$-restricted; Hogquist, K. A. et al., *Cell* 76: 17-27 (1994)] and OT-II [Ovalbumin 326-339-specific, H-2A$^b$-restricted; Barnden, M. J. et al., *Immunol. Cell Biol.* 76: 34-40 (1998)] transgenic mice. Wild-type CD4+ V$\alpha$2+ OT-II T cells expanded poorly in RAG$^{-/-}$ mice, consistent with previous reports indicating that these cells show little homeostatic expansion in lymphopenic hosts. Ernst, B. et al., *Immunity* 11: 173-181 (1999). In contrast, this limitation did not apply to T cells from LAG-3$^{-/-}$ OT-II transgenic mice, which expanded vigorously in lymphopenic hosts to numbers that were 3.2-fold more that the wild-type T cells by 15 days post-transfer. Similarly, the number of LAG-3$^{-/-}$ CD8+ V$\alpha$2+ OVA transgenic T cells recovered from RAG-1$^{-/-}$ mice was 4-fold higher than wild-type control OVA T cells. Remarkably, this difference persisted for at least a month post transfer. These data again demonstrated that both CD4+ and CD8+ T cells are equally affected by the loss of LAG-3. To assess the importance of LAG-3 ligation by MHC class II molecules, LAG-3$^{-/-}$ and wild type OVA transgenic T cells were transferred into mice lacking both MHC class I and class II molecules ($\beta$2m$^{-/-}$×H-2A$\beta^{b-/-}$). The data clearly show that the enhanced expansion of LAG-3$^{-/-}$ T cells is abrogated in the absence of MHC class II molecules, demonstrating the importance of this interaction.

LAG-3$^{-/-}$ mice or adoptive recipients of LAG-3$^{-/-}$ T cells have increased numbers of cells that are normally negative for LAG-3, such as B cells and macrophages. This supports the idea that an alteration in the homeostatic control of T cells, due to the absence of LAG-3, directly alters the control of other leukocyte cell types. To test this directly, B cells were co-transferred with either LAG-3$^{-/-}$ or wild-type T cells into RAG$^{-/-}$ mice. We also took advantage of this approach to assess the contrasting roles of MHC class II molecules in regulating T cells homeostasis. Previous studies have clearly demonstrated that the homeostatic expansion and long-term survival of CD4+ T cells requires periodic interaction with MHC class II molecules. Takeda, S. et al., *Immunity* 5: 217-228 (1996); Rooke, R., et al., *Immunity* 7:123-134 (1997). In contrast, it is possible that the interaction between LAG-3 and MHC class II molecules would have the opposite effect. As seen previously, there was a 3.0-fold increase in the number of LAG-3$^{-/-}$ T cells compared with the wild type control when transferred with MHC class II$^{-/-}$ B cells. However in the presence of wild-type B cells, the difference between LAG-3$^{-/-}$ and LAG-3$^{+/+}$ T cell numbers increased to 4.9-fold. The increased LAG-3$^{-/-}$ T cell number is likely due to increased MHC: TCR interaction, thus potentiating expansion. In contrast, the LAG-3$^{+/+}$ T cells would be subjected to both positive (via MHC:TCR interaction) and negative (via MHC:LAG-3 interaction) homeostatic control which results in comparable expansion of wild-type T cells.

In the presence of wild-type T cells, the number of B cells recovered from the spleen 7 days post-transfer was identical to mice receiving B cells alone. In contrast, there was a 2.7-fold increase in the number of B cells recovered from LAG-3$^{-/-}$ T cell recipients, providing a direct demonstration that the increased B cell number was due to the 'deregulation' of LAG-3$^{-/-}$ T cells. Interestingly, there was an increase in the number of MHC class II$^{-/-}$ B cells in the presence of wild-type T cells compared with mice receiving B cells alone. This supports the idea that the 'local' absence of LAG-3:MHC class II interaction can result in increased B cell expansion due to transient deregulation of wild-type T cells even though the recipient RAG$^{-/-}$ mice have MHC class II$^+$ macrophages and dendritic cells in the spleen. An alternate possibility is that ligation of MHC class II molecules by LAG-3 delivers a negative regulatory signal to B cells thereby preventing expansion. While this is plausible for B cells, it would not explain the increased numbers of MHC class II$^-$ cells, such as granulocytes, in LAG-3$^{-/-}$ mice. One possibility, which is currently being investigated, is that the deregulated expansion of LAG-3$^{-/-}$ T cells results in their production of cytokines that induce the broad expansion of many cell types.

The influence of LAG-3 expression on homeostatic expansion in lymphopenic mice is not limited to naïve T cells. Transfer of antigen-experienced 'memory' OT-II T cells also resulted in a substantially accelerated expansion of LAG-3$^{-/-}$ T cells compared with the wild-type control cells [7.2-fold]. It was important to verify that LAG-3 was directly responsible for this 'deregulated' T cells expansion and not a closely linked gene that was disrupted by the original targeting strategy. Thus, LAG-3$^{-/-}$ OT-II T cells were transduced with murine stem cell virus (MSCV)-based retrovirus that contained either wild-type LAG-3 or a signaling defective mutant, LAG-3.ΔK$^M$. Workman, C. J. et al., *Eur. J. Immunol.* 32: 2255-2263 (2002). The vector also contained an internal ribosomal entry site (IRES) and green fluorescent protein (GFP) cassette to facilitate analysis of transduced cells. Persons, D. A. et al., *Blood* 90: 1777-1786 (1997). LAG-3$^{-/-}$ and LAG-3$^{+/+}$ OT-II T cells were also transduced with an 'empty' vector/GFP alone control. Transduced cells were transferred into RAG-1$^{-/-}$ recipients and the number of OT-II T cells recovered 15-days post-transfer determined. As expected, the LAG-3$^{-/-}$ GFP alone control T cells expended more than the wild-type GFP cells [2.8-fold]. Ectopic expression of LAG-3 reduced the number of OT-II T cells to a level comparable to the wild-type control, while expression of the LAG-3 signaling defective mutant had no effect on homeostatic expansion. These data demonstrate that LAG-3 is directly responsible for the effects observed.

Our data clearly show that LAG-3 negatively regulates homeostatic expansion of T cells. They also support the idea that T cells may contribute to the homeostasis of many cell types. Despite the clear effect that the absence of LAG-3 had on T cells numbers in knockout mice and the expansion of T cells in lymphopenic mice, it was remarkable that only a very small percentage of T cells expressed LAG-3. Interestingly, ectopic expression of LAG-3 on all T cells did not have a greater effect on homeostatic expansion than the low-level, transient expression of LAG-3 seen on wild-type cells. This suggests that the threshold for LAG-3 signaling may be very low, and that there may be other factors that limit the effect of LAG-3 signaling. Identifying the downstream signaling molecules(s) that interact with LAG-3 and determining the mechanism by which LAG-3 regulates homeostatic expansion will clearly be an important focus of future research.

A surprising observation was the increased number of cells that do not express LAG-3, such as B cells and macrophages. Co-transfer experiments clearly demonstrated that the absence of LAG-3 on T cells was responsible for the increase in other cells types observed. This could be due to a soluble or cell surface protein that is either induced by LAG-3 signaling that limits the number and/or expansion of other cell types or produced due to the absence of negative regulation by LAG-3 that limits the number and/or expansion of other cell types. The precise nature of this bystander expansion and its physiological role remain to be determined.

Patients receiving bone marrow or mega dose stem cell transplants are particularly susceptible to infections in the first 4-6 months due to the slow rate of lymphocyte reconstitution. Our studies support the idea that LAG-3 is a viable therapeutic target and that blocking LAG-3 expression or function will accelerate T cell engraftment and significantly reduce this window of susceptibility.

Example 2

Materials and Methods

This example provides the experimental methods and materials for example 1.

Mice:

The following mice were used: LAG-3$^{-/-}$ [obtained from Yueh-Hsiu Chen, Stanford University, Palo Alto, Calif., with permission from Christophe Benoist and Diane Mathis, Joslin Diabetes Center, Boston, Mass.; Miyazaki, T. et al., *Science* 272: 405-408 (1996)]; C57BL/6J [Jackson Labs, Bar Harbor, Me.]; B6.PL-Thy1$^a$/Cy (Thy1.1 congenic) [Jackson Labs]; RAG-1$^{-/-}$ [Jackson Labs, Bar Harbor, Me.; Mombaerts, P. et al., *Cell* 68: 869-877 (1992)]; MHC class II$^{-/-}$ [provided by Peter Doherty, St. Jude Children's Research Hospital, Memphis, Tenn.; Grusby, M. J. et al., *Science* 253: 1417-1420 (1991)]; MHC class I$^{-/-}$/II$^{-/-}$ [Taconic, Germantown, N.Y.; Grusby, M. J. et al., Proc. Natl. Acad. Sci. U.S.A 90: 3913-3917 (1993)]; OT-II TCR transgenic mice [provided by Stephen Schoenberger, La Jolla Institute for Allergy and Immunology, La Jolla, Calif., with permission from William Heath, Walter and Eliza Hall Institute, Parkville, Victoria Australia; Barnden, M. J. et al., *Immunol. Cell Biol.* 76: 34-40 (1998)] and OT-I (OVA) TCR transgenic mice [Jackson Labs; Hogquist, K. A. et al., *Cell* 76: 17-27 (1994)]. Genome-wide microsatellite analysis demonstrated that 97% of the 88 genetic markers tested for the LAG-3$^{-/-}$ mice were derived from B6 mice (Charles River Laboratories, Troy, N.Y.). LAG-3$^{-/-}$, MHC class II$^{-/-}$, OT-I.LAG-3$^{-/-}$ and OT-II.LAG-3$^{-/-}$ colonies were maintained in the St. Jude Animal Resource Center. All animal experiments were performed in an AAA-LAC-accredited, SPF facility following national, state and institutional guidelines. Animal protocols were approved by the St. Jude IACUC.

LAG-3 Constructs and Retroviral Transduction:

LAG-3 constructs were produced using recombinant PCR as described (Vignali, D. A. A. and K. M. Vignali, *J. Immunol.* 162: 1431-1439 (1999)). The LAG-3.WT and LAG-3.ΔK$^M$ (LAG-3 with a deletion of the conserved KIEELE motif in the cytoplasmic tail) have been described (Workman, C. J. et al., *J. Immunol.* 169: 5392-5395 (2002)). LAG-3 constructs were cloned into a murine stem cell virus (MSCV)-based retroviral vector, which contained an internal ribosomal entry site (IRES) and green fluorescent protein (GFP), and retrovirus produced as described (Persons, D. A. et al., *Blood* 90: 1777-1786 (1997); Persons, D. A. et al., *Blood Cells Mol Dis.* 24: 167-182 (1998)). Retroviral producer cell lines were generated by repeatedly transducing GPE+86 cells (7-10) times until a viral titer of greater then 10$^5$/ml after 24 hr was obtained (Markowitz, D. et al., *J Virol.* 62: 1120-1124 (1988)).

Flow Cytometry:

Single cell suspensions were made from spleens and RBC lysed with Gey's solution. Splenocytes were first stained with Fc Block, anti-CD16/CD32 (2.4G2) (BD PharMingen, San Diego, Calif.) for 10 min on ice. The cells were then stained for the following cell surface markers using various conjugated antibodies from BD PharMingen: αβ+ TCR(H-57-

597), Vα2 (B20.1), γδ TCR (GL3), CD4 (RM4-4), CD8a (53-6.7), CD45R/B220 (RA3-6B2), CD11b/Mac1 (M1/70), Gr-1 (RB6-8C5), CD44 (IM7), CD25/IL2R (7D4), CD69 (H1.2F3) and CD244.2/NK cells (2B4). LAG-3 expression was assessed with a biotinylated rat anti-LAG-3 mAb (C9B7W, IgG1 κ; Workman, C. J. et al., *Eur. J. Immunol.* 32: 2255-2263 (2002)) or the same antibody obtained as a PE conjugate (BD PharMingen). The cells were then analyzed by flow cytometry (Becton Dickinson, San Jose, Calif.).

Bromodeoxyuridine Incorporation:

At 5, 16, 28, and 52 weeks of age, LAG-3$^{+/+}$, LAG-3$^{-/-}$, OTII.LAG-3$^{+/+}$ and OTII.LAG-3$^{-/-}$ mice were given BrdU (Sigma, St. Louis, Mo.) in their drinking water for 8 days (0.8 mg/ml). The mice were then sacrificed by $CO_2$ inhalation and the spleens removed. Staining for BrdU incorporation was performed as described (Flynn, K. J. et al., *Proc. Natl. Acad. Sci. U.S.A* 96: 8597-8602 (1999)). Briefly, the LAG-3$^{-/-}$ and LAG-3$^{+/+}$ splenocytes were stained for TCRαβ, CD4, CD8 and B220 expression. The OTII.LAG-3$^{+/+}$ and OTII.LAG-3$^{-/-}$ splenocytes were stained for Vα2 and CD4 expression (PharMingen). The cells were then fixed with 1.2 ml ice-cold 95% ethanol for 30 min on ice. The cells were washed and permeabilized with PBS+1% paraformaldehyde+0.01% Tween 20 for 1 h at room temperature. The cells were then washed and incubated with 50 KU of DNase (Sigma) in 0.15M NaCl+4.2 mM $MgCl_2$ pH 5.0 for 10 min at 37° C. BrdU was detected by the addition of anti-BrdU-FITC (Becton Dickinson) for 30 min at RT and then analyzed by flow cytometry.

Adoptive Transfer Experiments:

T cells and/or B cells from splenocytes were either positively sorted by FACS or negatively sorted by magnetic bead cell sorting (MACS). For FACS purifications, splenocytes were stained for TCR, CD4 and CD8 expression and sorted by positive selection on a MoFlow (Cytomation, Ft. Collins, Colo.). For negative MACS purification, splenocytes were stained with PE-coupled anti-B220, anti-Gr1, anti-Mac1, anti-TER119 (erythrocytes), anti-CD244.2 (NK cells) and anti-CD8 (for negative purification of DTII transgenic T cells). The cells were then incubated with magnetic beads coupled with anti-PE antibody (Miltenyi Biotech, Auburn, Calif.) and then negatively sorted on an autoMACS (Miltenyi Biotech, Auburn, Calif.) to 90-95% purity. In some experiments, T cells were labeled with carboxyfluorescein diacetate succinimidyl ester (CFSE). Cells were washed twice with PBS, resuspended in PBS plus 0.1% BSA at $1\times10^7$ cells/ml and incubated with 5 µM CFSE for 10 min at 37° C. The cells were washed twice with PBS plus 0.1% BSA. The purified CFSE labeled or unlabeled T cells ($5\times10^6$ or $1\times10^7$) and in some cases B cells ($5\times10^6$) were injected i.v. into RAG-1$^{-/-}$ or Thy1.1$^+$ (B6.PL) mice.

Retroviral Transduction of Normal T Cells:

Spleens from OTII.LAG-3$^{+/+}$ and OTII.LAG3$^{-/-}$ mice were removed and single cell suspensions made at $2.5\times10^6$ cell/ml. The splenocytes were activated with OVA 326-339 peptide [10 µM] in culture for two days. The activated splenocytes were then incubated on a monolayer of GFP alone, LAG-3.WT/GFP or LAG-3.ΔK$^M$/GFP retroviral producer cells for 2 days in the presence of polybrene. The cells were allowed to rest for 10 days and then sorted for Vα2$^+$/CD4$^+$/GFP$^+$ expression by FACS. The cells were allowed to rest for two additional days and then $5\times10^6$ cells were injected into RAG$^{-/-}$ mice via the tail vein. Fifteen days post-transfer, the mice were sacrificed by $CO_2$ inhalation and the spleens removed. The splenocytes were stained and analyzed by flow cytometry.

Example 3

Induced Treg Cells with Potent Regulatory Activity

In order to identify Treg specific molecules, we performed a differential gene expression analysis of antigen-specific T cells differentiating to either effector/memory cells in response to viral infection or Treg cells upon encounter of cognate antigen as a self-antigen. This analysis revealed that the LAG-3 gene was selectively upregulated in Treg cells. The physiologic role of LAG-3, an MHC class II binding CD4 homologue, has not been clearly elucidated. Several in vitro studies have suggested that LAG-3 may have a negative regulatory function (Hannier et al., 1998; Huard et al., 1994; Workman et al., 2002a; Workman et al., 2002b). Here we show that membrane expression of LAG-3 selectively marks Treg cells independently of CD25 and that LAG-3 modulates both the in vitro and in vivo suppressive activity of Treg cells.

In order to study differences between T cell effector/memory and tolerance induction, we have utilized adoptive transfer of T cell receptor (TCR) transgenic CD4+ T cells (clone 6.5) specific for a model antigen-hemagglutinin (HA). In wild-type mice infected with recombinant HA-expressing vaccinia virus (Vac-HA), adoptively transferred HA specific 6.5 CD4+ T cells differentiate into effector/memory cells upon encounter with HA. The effector/memory response is characterized by a typical expansion/contraction phase and the development of memory markers. When removed from the adoptively transferred animal, these effector/memory cells are hyper-responsive to HA in vitro relative to naive 6.5 CD4+ T cells as assayed by antigen-specific proliferative response and γ-interferon production. This memory response persists for months after adoptive transfer. In contrast, adoptive transfer of 6.5 CD4+ T cells into C3-HA transgenic mice, that express HA in multiple epithelial tissues, results in tolerance (Adler et al., 2000; Adler et al., 1998). Similar to the effector/memory response, there is a rapid expansion/activation phase characterized by proliferation and expression of effector cytokines, such as γ-interferon. However, after the activation phase, the total HA-specific T cell pool contracts and residual 6.5 cells fail to produce γ-interferon or proliferate in vitro upon antigen stimulation 4-7 days after adoptive transfer (Adler et al., 2000; Huang et al., 2003). The extinction of the capacity to produce lymphokines such as IL-2 and γ-interferon and proliferate in response to antigen represents the standard operational definition of the anergic phenotype.

The intensity of the initial in vivo effector phase in C3-HA mice that precedes tolerance induction, is proportional to the number of 6.5 CD4+ T cells adoptively transferred as well as the expression level of HA antigen in the recipient mice. Thus, C3-HA$^{low}$ mice tolerate the transfer of $2.5\times10^6$ 6.5 CD4+ T cells quite well, but C3-HA$^{high}$ mice, which have 1000 fold higher HA expression than C3-HA$^{low}$ mice, die within 4-7 days after transfer of $2.5\times10^6$ 6.5 CD4+ T cells (FIG. 1A). The cause of death is lethal pulmonary vasculitis due to infiltration of transgenic 6.5 CD4+ T cells in the lung, where HA expression is the highest. Adoptive transfer of less than $2.5\times10^5$ 6.5 CD4+ T cells into C3-HA$^{high}$ mice causes pulmonary vasculitis of less severity and the recipients survive (FIG. 1A) (Huang et al., 2003). Interestingly, 6.5 CD4+ T cells transferred at a sublethal dose acquire a regulatory phenotype as they are capable of protecting mice from death upon subsequent infusion of what would be a lethal dose of 6.5 CD4+ T cells in unprotected C3-HA$^{high}$ mice. This in vivo regulatory function is extremely potent, since transfer of as few as 8,000 cells (0.3% of the lethal dose) will completely protect animals from death upon subsequent infusion of 2.5×

10⁶ naive 6.5 CD4+ T cells. Protection is observed as early as 4 days after the initial transfer and remains active up to 6 months (FIG. 1A). Depletion of CD4+ T cells, but not CD8+ T cells, before adoptive transfer totally eliminates the protective effect, thereby defining the Treg phenotype of anergized clonotypic 6.5 CD4+ T cells.

Figure 1B:
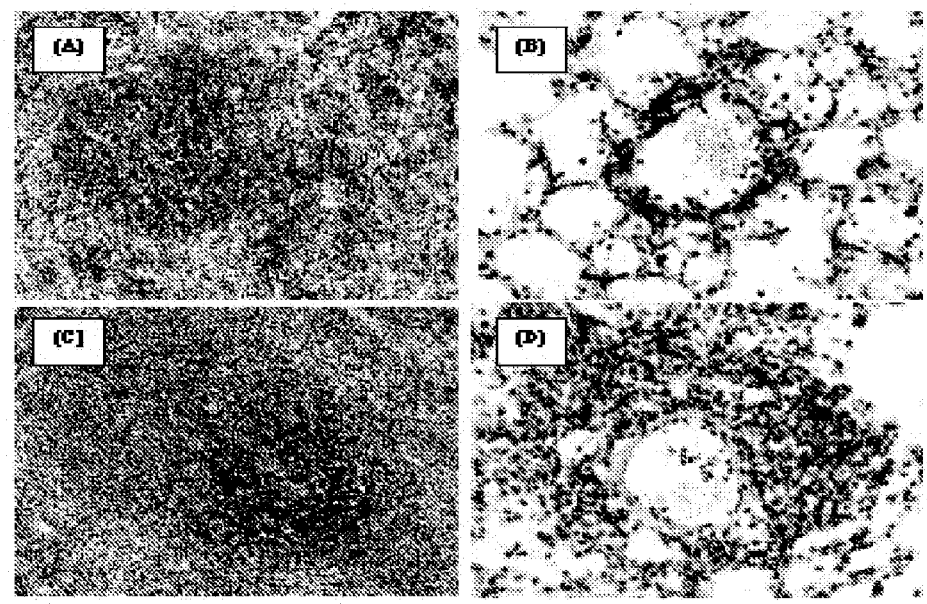

Suppression of lethal pneumonitis is accompanied by an accumulation of the initial input (Treg) 6.5 T cells in the lungs and a drastic reduction in the number of infiltrating T effector cells from the second infusion. Instead of accumulating in the lungs, as occurs in the absence of Treg cells, the T effector cells accumulate in the splenic peri-arteriolar lymphatic sheath (FIG. 1B). Further evidence that the anergic cells demonstrate Treg function comes from the finding that they inhibit the activation of cytotoxic HA-specific CD8+ T cells in vivo (data not shown). Elimination of CD25+ T cells prior to the first (protective) adoptive transfer did not affect the development of Treg cells capable of protecting animals from a subsequent lethal challenge of 6.5 T cells. Therefore, it is likely that the Treg phenotype of the initial input T cells was acquired after adoptive transfer as opposed to being a consequence of naturally occurring Treg cells among the adoptively transferred population. These findings are highly compatible with the published findings of Von Boehmer and colleagues, who demonstrated that 6.5 CD4+ T cells rendered tolerant after transfer into transgenic mice expressing HA in the B cell compartment in fact exhibit Treg function (Jooss et al., 2001).

Example 4

LAG-3 is Differentially Expressed on Induced Treg Cells

In order to identify genes associated with the anergic/Treg phenotype in our in vivo system, we performed Affymetrix chip analysis on purified 6.5 CD4+ T cells either after adoptive transfer into non-transgenic recipients followed by Vac-HA immunization to generate effector/memory T cells or after transfer into C3-HA$^{high}$ mice to generate anergic/Treg cells. Thy1.1(+)Thy1.2(−) congenic 6.5 T cells were purified from Thy1.1(−)Thy1.2(+) Vac-HA infected wild-type (effector/memory) or C3HA$^{high}$ (anergic/Treg) recipients using a sequential isolation procedure involving MACS Column depletion of CD8+ T cells, B cells and Thy 1.2(+) T cells followed by flow cytometric sorting to >95% purity. This protocol avoids the use of TCR-specific or CD4 coreceptor specific antibodies that could potentially alter TCR or CD4 dependent gene expression patterns.

Figure 2A:
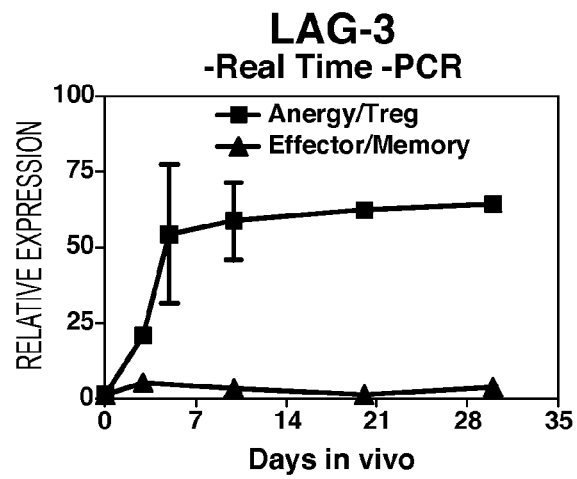
FIG. 2A-2C. LAG-3 is differentially expressed between anergic/Treg and effector/memory CD4+ T cells and LAG-3 expression in anergic/Treg CD4+ T cells is correlated with IL-10 expression. The differential expression revealed by gene chip analysis was confirmed by (FIG. 2A) quantitative real-time RT-PCR. The differential expression of LAG-3 in earlier days (Day 2 to Day 4) extends to 30 days after adoptive transfer.

RNA was isolated from naive 6.5 CD4+ T cells as the day 0 sample and isolated from 6.5 CD4+ T cells at days 2, 3 and 4 post-adoptive transfer for chip analysis. Genes that were differentially expressed between anergic/Treg populations and effector/memory populations were rank ordered according to an algorithm that summed their differential expression from days 0-4. A surprisingly large number of genes were selectively activated in anergic/Treg populations even at these early time points post adoptive transfer. Many of these genes represented ESTs with no known function. Among the genes that had been previously identified, LAG-3 was among the most differentially expressed in anergic/Treg populations relative to effector/memory populations. This result was subsequently validated by quantitative RT-PCR analysis with a LAG-3 primer-probe pair for various time points extended to 1 month post adoptive transfer. After a minimal initial increase in the effector/memory cells, LAG-3 expression returns to baseline by 20 days post adoptive transfer. In striking contrast, LAG-3 expression increases 20-50 fold over the first 5 days among anergic/Treg cell populations and remains high over the subsequent 4-week analysis (FIG. 2A). In contrast, levels of FoxP3, GITR and CTLA-4 showed modest increases (1.5-4 fold) that were similar in both effector/memory cells and the induced anergic/Treg cells over the first 4-5 days (data not shown).

Figure 2B:
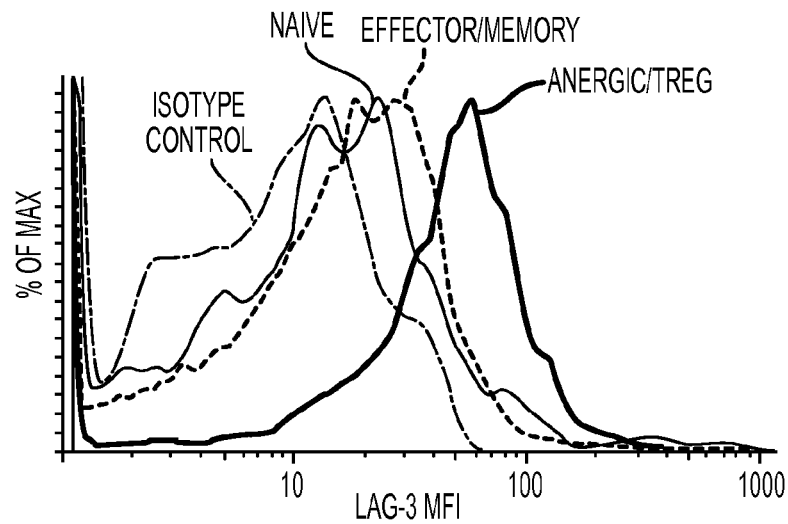
Figure 2C:
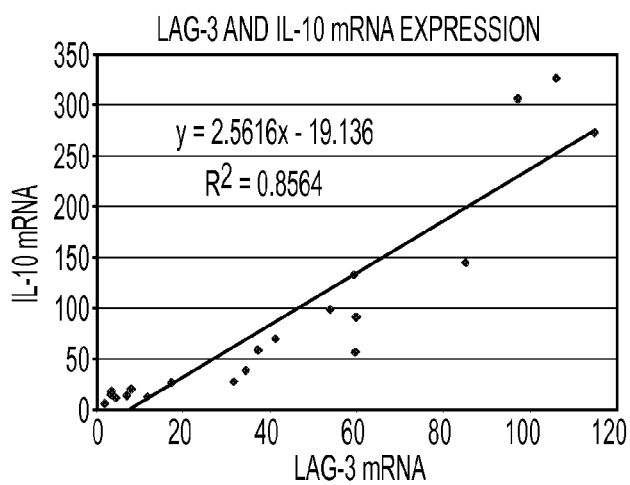

Cell surface expression of LAG-3 on populations of anergic/Treg 6.5 CD4+ T cells relative to effector/memory 6.5 CD4+ T cells was then analyzed using an anti-LAG-3 monoclonal antibody (Workman et al., 2002b) (FIG. 2B). While there are very low levels of LAG-3 staining on effector/memory cells, a significant proportion of anergic/Treg cells from C3-HA$^{high}$ transgenic mice display moderate to high levels of LAG-3 staining, correlating with the gene expression results. As IL-10 is commonly associated with differentiation and function of Treg (Moore et al., 2001), we analyzed the endogenous levels of IL-10 mRNA and their correlation to the levels of LAG-3 mRNA in CD4+ T cell subsets from C3-HA$^{high}$ transgenic mice (anergic/Treg 6.5 CD4+ T cells). Analysis of multiple samples of anergic/Treg populations over many experiments revealed correlation between LAG-3 mRNA level and IL-10 mRNA level with a correlation coefficient ($R^2$) of 0.87 (FIG. 2C).

Example 5

LAG-3 is Required for Maximal Treg Function

Figure 3A:
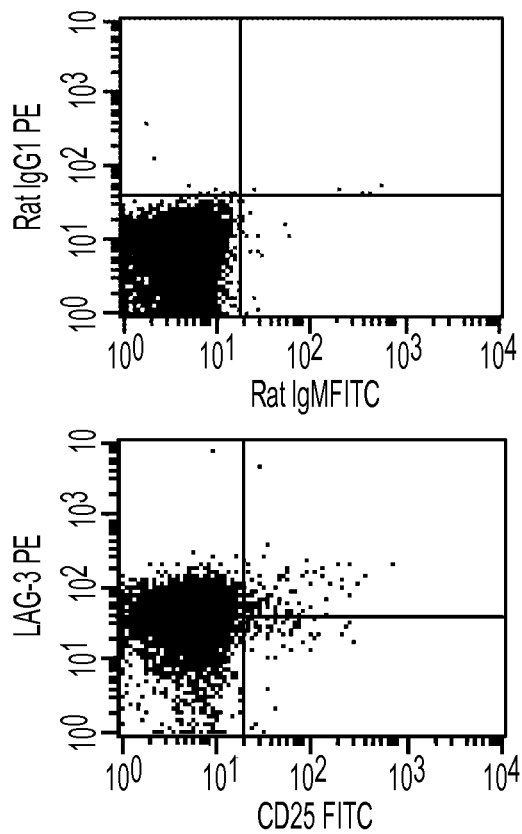
FIG. 3A-3B. LAG-3 is expressed on induced Treg cells independently of CD25 and is a marker of Treg function.
Figure 3B:
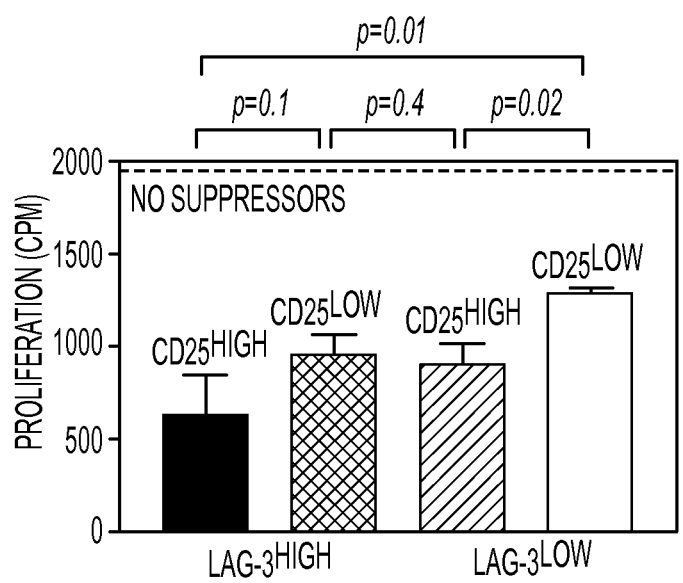

Cell surface expression of LAG-3 and CD25 on populations of anergic/Treg 6.5 CD4+ T cells was analyzed coordinately using anti-LAG-3 and anti-CD25 monoclonal antibodies. Although similar proportions of effector/memory and anergic/Treg cells express CD25 (data not shown), LAG-3 and CD25 expression on anergic/Treg cells was not completely concordant (FIG. 3A). We therefore sorted the cells into LAG-3$^{high}$CD25$^{high}$, LAG-3$^{high}$CD25$^{low}$, LAG-3$^{low}$/CD25$^{high}$, and LAG-3$^{low}$CD25$^{low}$ populations and analyzed their regulatory activity in a standard in vitro suppression assay. In vitro suppression of proliferative responses among naive 6.5 CD4+ cells showed that the LAG-3$^{high}$CD25$^{high}$ population displayed the highest suppressive activity and the LAG-3$^{low}$CD25$^{low}$ population had the lowest while the suppressive activity of the LAG-3$^{high}$CD25$^{low}$ and the LAG-3$^{low}$/CD25$^{low}$ cells were comparable (FIG. 3B). These results suggest that, among induced Treg cells, the combination of LAG-3 and CD25 may mark Treg cells with the most suppressive activity.

Figure 4:
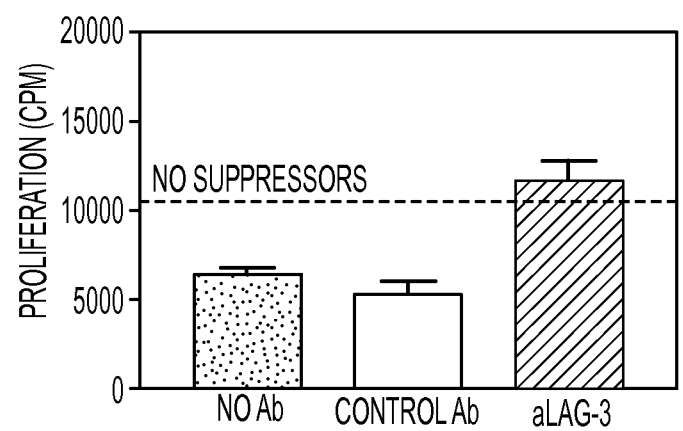
FIG. 4. Anti-LAG-3 antibodies block in vitro Treg activity. Monoclonal anti-LAG-3 antibody added to the in vitro suppression assay at a concentration of 2 μg/ml, totally reverses the suppression of naïve 6.5 CD4+ T cell proliferation in vitro by 6.5 CD4+ suppressors at a suppressor: responder ratio of 0.04:1.

To further evaluate the direct role of LAG-3 in regulating suppression by induced Treg cells, we first determined whether anti-LAG-3 antibodies could block the ability of LAG-3 expressing cells to suppress the in vitro proliferative responses of naive HA-specific T cells. Anti-LAG-3 antibodies at the concentration of 2 μg/ml inhibit suppression by Treg 6.5 CD4+ T cells in the in vitro assay system (FIG. 4). Over the 2-day assay period, anti-LAG-3 antibodies did not affect proliferative responses of 6.5 T cells stimulated in the absence of Treg, confirming that the effect of anti-LAG-3 antibodies was indeed on the Treg cells and not the effector cells (data not shown). The ability of anti-LAG-3 antibodies to block in vitro suppression by Treg cells demonstrates that LAG-3 is not simply a Treg selective marker, but is a molecule that modulates Treg activity.

Example 6

LAG-3 is Required for Induced Treg Activity In Vivo

Figure 5A:
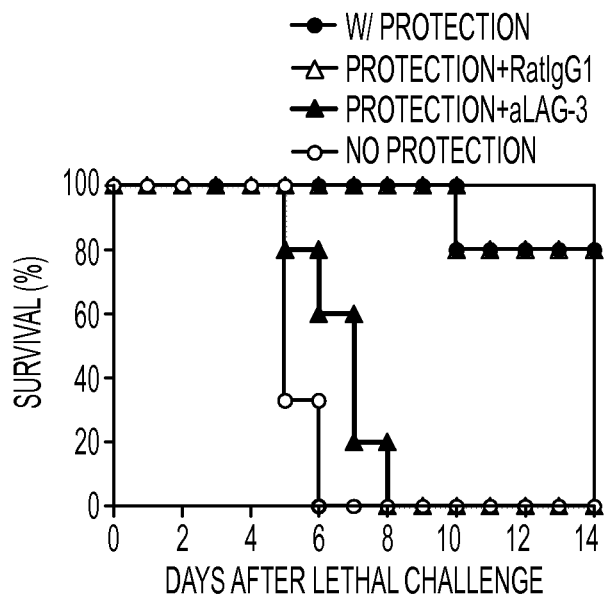
FIG. 5A to 5C. Anti-LAG-3 antibody eliminates the in vivo suppression by 6.5 CD4+ Treg cells by directly inhibiting Treg cells.
Figure 5B:
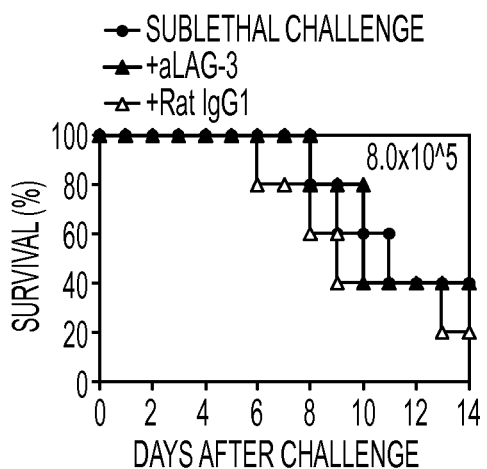

We next evaluated the role of LAG-3 in modulating in vivo Treg function by determining whether administration of anti- LAG-3 antibodies could block suppression of lethal pneumonitis by Tregs in C3-HA$^{high}$ mice. C3-HA$^{high}$ mice were pretreated with 8,000 (sublethal dose) of 6.5 CD4+ T cells followed by a subsequent dose of 2.5×10$^6$ naive 6.5 CD4+ T cells 4 days after the first transfer. As described above, Tregs have already developed at this point. Anti-LAG-3 antibody (200 g) was administered i.v. together with the subsequent challenge of 2.5×10$^6$ 6.5 cells and another 200 g was given 2 days later. This antibody treatment totally eliminated the in vivo suppressive activity of the Treg cells and the mice died in a time frame comparable to the C3-HA$^{high}$ mice lethally challenged without protective sublethal 6.5 pretreatment. On the contrary, mice with established Treg treated with isotype control antibody (Rat IgG1) or no antibody survived subsequent challenge with 2.5×10$^6$ naive 6.5 T cells (FIG. 5A). While these results suggest that the anti-LAG-3 antibodies were blocking Treg activity in vivo, an alternate formal possibility was that, rather than directly inhibiting Treg cells, the anti-LAG-3 antibodies hyper-activated the T cells in the challenge population such that they overcame the inhibitory effects of the Tregs. To rule out this possibility, we asked whether in vivo administration of anti-LAG-3 antibodies together with a dose of 6.5 T cells just below the lethality threshold would cause lethality in the absence of a pre-established Treg population. We therefore administered 2.5×10$^5$ 6.5 T cells (the maximal dose that will not cause lethality) or 8.0×10$^5$ 6.5 T cells (roughly 50% lethality between 7 and 14 days after transfer) into C3-HA$^{high}$ mice together with anti-LAG-3 antibodies or isotype control. FIG. 5B demonstrates that the anti-LAG-3 treatment did not render the 2.5×10$^5$ 6.5 T cell dose lethal nor enhance the partial lethality of the 8.0×10$^5$ 6.5 T cell dose. Therefore, the effect of anti-LAG-3 antibodies in the experiment in FIG. 5A was to directly inhibit Treg cells.

Example 7

Figure 6A:
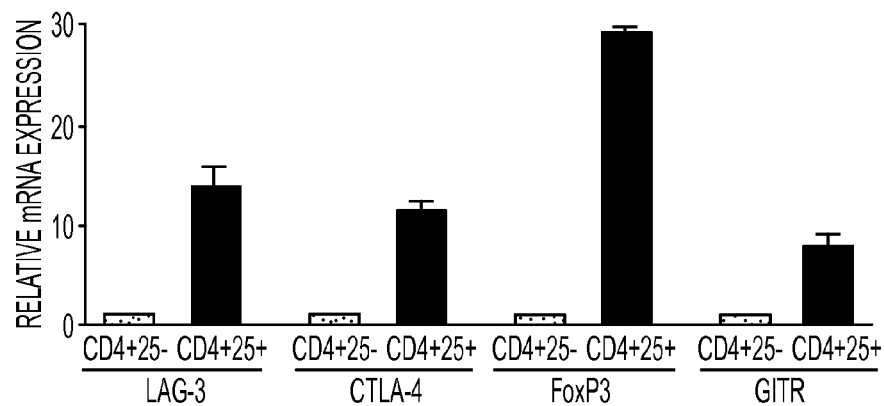
FIG. 6A to 6D. Role of LAG-3 in natural CD4+CD25+ T cells.
Figure 6B:
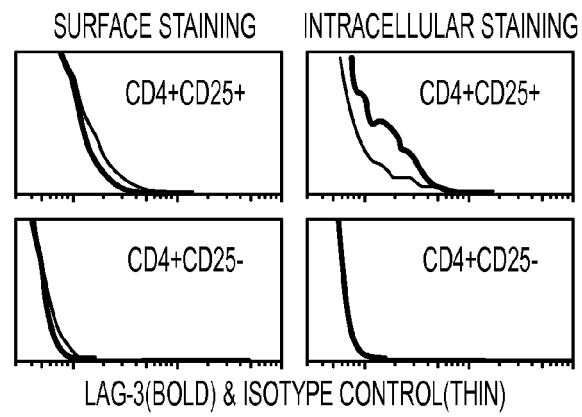
Figure 6C:
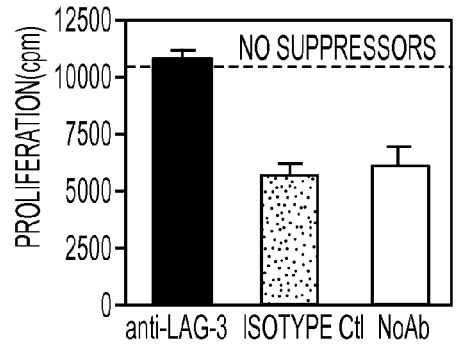
Figure 6D:
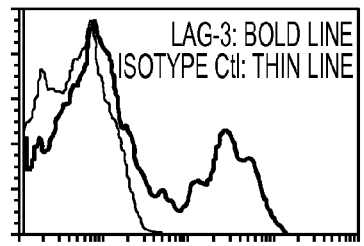

LAG-3 is Expressed by Natural Treg Cells and is Required for Suppressor Activity Taken together, these data confirm an important role for LAG-3 in mediating suppressor function of induced Treg. Given that the relationship between induced Treg and natural Treg remains unclear, it was of interest to see whether LAG-3 was expressed selectively on CD4+CD25+ T cells from wild type mice. LAG-3 mRNA (along with CTLA-4, FoxP3 and GITR mRNA) is indeed selectively expressed on CD4+CD25+ cells compared with CD4+CD25− cells (FIG. 6A). Despite this reproducible finding, we were unable to detect surface LAG-3 on either CD4+CD25+ or CD4+CD25− cells by antibody staining However, antibody staining of permeabilized cells clearly indicated that 10-20% of CD4+CD25+ cells expressed intracellular stores of LAG-3. In contrast staining of permeabilized CD4+CD25− cells demonstrated absolutely no LAG-3+ population (FIG. 6B). These findings suggested that at least some natural Tregs possessed intracellular stores of LAG-3 that could be rapidly recruited to the cell surface upon encounter with cognate antigen and subsequently mediate suppression. While natural Treg are contained within the T cell population defined by CD4 and CD25, it is indeed possible that the actual Treg cells are those expressing intracellular LAG-3. To directly evaluate the role of LAG-3 in the regulatory function of natural Tregs, we asked whether anti-LAG-3 antibodies could inhibit in vitro suppression mediated by purified CD4+CD25+ cells. FIG. 6C demonstrates that anti-LAG-3 antibodies indeed block suppression mediated by purified CD4+CD25+ cells, suggesting that LAG-3 plays a role in suppression mediated by natural as well as induced Treg. Staining of the CD4+CD25+ cells at the end of the in vitro suppression assay revealed that roughly 20% now express high levels of LAG-3 on their surface, supporting the notion that the intracellular LAG-3 in mobilized to the surface under circumstances of TCR engagement and mediates regulatory activity (FIG. 6D).

Example 8

Ectopic Expression of LAG-3 Confers Regulatory Activity

Figure 5C:
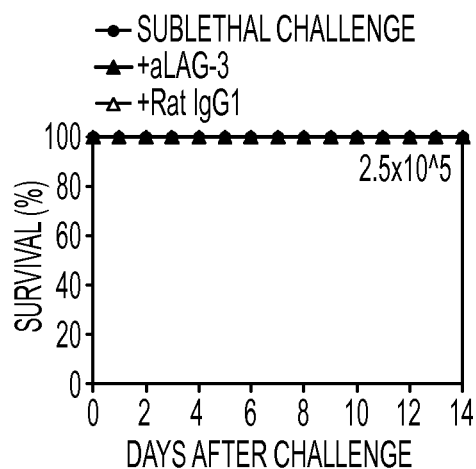
Figure 7:
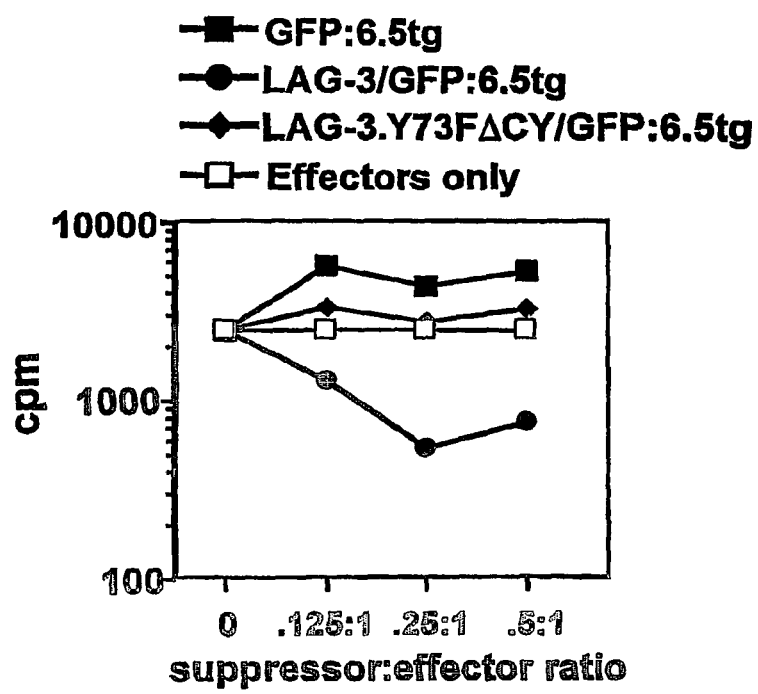
FIG. 7. Ectopic expression of wild type but not mutant LAG-3 in CD25 depleted 6.5 CD4+ T cells confers potent in vitro regulatory activity. 6.5 CD4+ T cells were first depleted of any CD25+"natural" Tregs and then transduced with MSCV-based retroviral vectors encoding either GFP alone, GFP+wild type LAG-3 or GFP+a mutant LAG-3.Y73FΔCY that has diminished binding to MHC class II and cannot mediate downstream signaling. After a 10 day rest period, essentially no endogenous LAG-3 staining was observed on GFP+ 6.5 CD4+ T cells transduced with the MSCV-GFP vector while high levels of LAG-3 staining were observed on GFP+ 6.5 cells transduced with the MSCV-LAG-3/GFP and MSCV-LAG-3.Y73FΔCY/GFP vectors. GFP+ cells from the MSCV-LAG-3/GFP and MSCV-LAG-3.Y73FΔCY/GFP transductions stained brightly with anti-LAG-3 antibodies while MSCV-GFP transduced cells displayed virtually no LAG-3 staining GFP+ cells from each group were sorted and mixed at different ratios with APC, 5 μg/ml HA110-120 peptide and naïve 6.5 CD4+CD25− cells in a proliferation assay.
Figure 8:
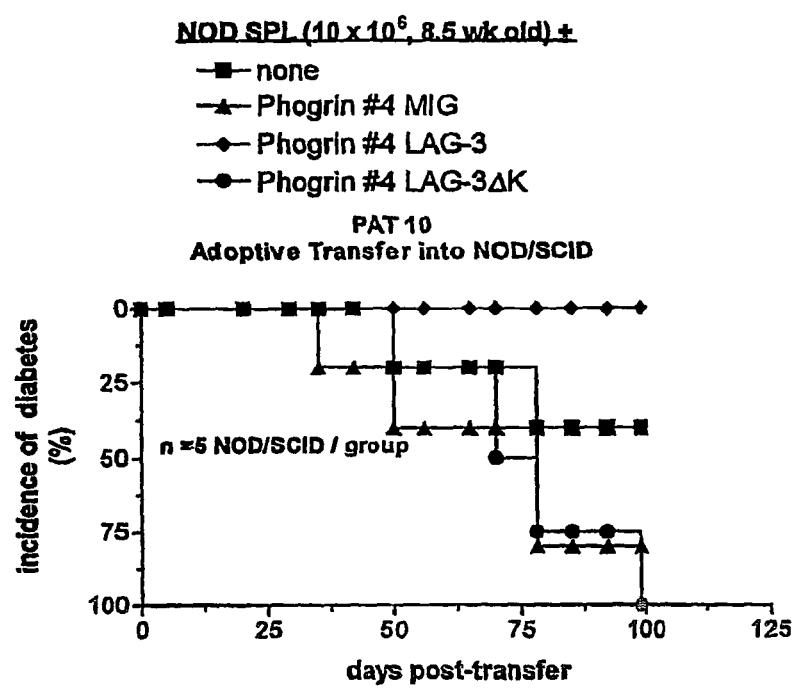
FIG. 8 shows that ectopic expression of LAG-3 on a Phogin-specific T cell clone confers protection from diabetes following co-transfer with splenyocytes from NOD mice. 10⁷ pre-diabetic NOD splenocytes were transferred alone (none)

The blocking experiments in FIGS. 5 and 6 suggest that LAG-3 is required for maximal Treg function. To further validate this conclusion, we performed a series of transduction experiments to determine if ectopic expression of LAG-3 on T cells confers regulatory activity. For these experiments, 6.5 CD4+ T cells were first depleted of any CD25+ "natural" Tregs and then transduced with MSCV-based retroviral vectors encoding either GFP alone, GFP+wild type LAG-3 or GFP+a mutant LAG-3.Y73FΔCY that has substantially reduced affinity for MHC class II and cannot mediate downstream signaling (Workman et al., 2002a). After a 10 day rest period, essentially no endogenous LAG-3 staining was observed on GFP+ 6.5 CD4+ T cells transduced with the MSCV-GFP vector while high levels of LAG-3 staining were observed on GFP+ 6.5 cells transduced with the MSCV-LAG-3/GFP and MSCV-LAG-3.Y73FΔCY/GFP vectors. GFP+ cells from each group were sorted and mixed at different ratios with APC, HA$^{110-120}$ peptide and naïve 6.5 CD4+CD25− cells in a proliferation assay. As shown in FIG. 7, 6.5 cells expressing wild type LAG-3 potently suppressed proliferation of naïve 6.5 cells while no suppression was observed with control GFP transduced 6.5 cells or 6.5 cells expressing the non-functional LAG-3.Y73FΔCY mutant. Total proliferation was in fact somewhat increased in these two latter groups, since GFP and LAG-3.Y73FΔCY transduced 6.5 cells themselves proliferate in addition to the naïve 6.5 cells in the assay. Indeed, wild type LAG-3 transduced T cells themselves demonstrated a significant reduction in proliferative responses apart from inhibiting proliferation of the non-transduced 6.5 cells. These results provide direct evidence confirming the functional role of LAG-3 in suppression. Interestingly, LAG-3 transduction did not induce other genes associated with Tregs, including Foxp3, CD25, CD103 and GITR (data not shown). This result, together with the lack of significant differential expression of these genes between 6.5 T cells differentiating to effector/memory vs anergic/Treg phenotypes, suggests that LAG-3 may mediate a distinct pathway of regulatory T cell function independent of the Foxp3 pathway.

Example 9

Discussion

These findings identify LAG-3 as a cell surface molecule selectively upregulated on Treg cells that may be directly involved in mediating Treg function. Given the many systems in which both natural and induced Treg activity has been defined, it remains to be determined whether LAG-3 is a "universal" Treg marker or selectively marks only certain Treg subsets. Our results suggest that in addition to induced CD4+ Treg cells, LAG-3 plays at least some role in mediating suppression by natural CD4+CD25+ Treg cells. Furthermore, other experimental data demonstrate a role for LAG-3 in the regulation of homeostatic lymphocyte expansion by natural Treg (Workman and Vignali, accompanying paper). The finding that LAG-3 expression is significantly greater among CD4+CD25+ T cells from wildtype mice suggests that it may play a role in the function of natural, as well as induced, Tregs. As suggested by the experiments in FIG. 3, the combination of LAG-3 and CD25 may define Treg subsets with the most potent suppressive activity. We do not propose that LAG-3 is a "lineage marker" for Treg as it is expressed at variable levels that correlate with the magnitude of regulatory activity in in vitro assays. In fact, it is not clear that Treg represent a stable lineage or differentiation state capable of promoting tolerance in a non-cell autonomous fashion (von Boehmer, 2003). Different mechanisms have been identified for Treg function in different systems (reviewed in Shevach, 2002). LAG-3$^{high}$ cells produce increased amounts of IL-10 and display enhanced in vitro suppressor activity but the role of IL-10 in mediating suppressive function in our system remains to be determined. Antibodies to LAG-3 inhibit the suppressor activity of Treg cells both in vitro and in vivo. We therefore propose that LAG-3 is a Treg specific receptor or coreceptor that modulates the suppressor activity of this T cell subset.

A number of studies have suggested a cell autonomous inhibitory role for LAG-3 (Huard et al., 1994; Workman et al., 2002b), although initial studies with LAG-3 KO mice failed to uncover any evidence for overt autoimmunity or hyperimmunity (Miyazaki et al., 1996). Given our proposed role for LAG-3 in Treg function, it might be expected that LAG-3 knockout mice would display multi-system autoimmunity (i.e., similar to Foxp3 knockout or scurfy mice), which has not been reported in these mice. However, there are clearly regulatory T cell defects displayed by LAG-3 knockout mice, such as a defect in regulating cellular homeostasis (Workman and Vignali, accompanying paper). We are in the process of reexamining older LAG-3 knockout mice for more subtle evidence of late-onset autoimmunity, as was observed in PD-1 knockout mice (Nishimura et al., 1999; Nishimura et al., 2001). It is also conceivable that other regulatory mechanisms might have been enhanced in these mice to compensate for the loss of LAG-3 expression.

Because it is expressed at higher levels on Treg cells, LAG-3 provides an excellent potential target for selective manipulation of Treg activity to treat both cancer and autoimmune disease. CD25, the "gold standard" Treg marker, is induced at high levels in activated cells, as it is a critical component of the IL-2 receptor complex. The apparent reason that CD4+CD25+ cells are enriched in Treg activity is not because CD25 is specific to Treg function, but rather because Treg cells are chronically stimulated by continuous encounter with self-antigen in the periphery. More recently, the TNF receptor super-family member 18 molecule (also called GITR) was demonstrated to be up-regulated on Treg cells. Furthermore, antibodies to GITR have been reported to inhibit Treg activity both in vivo and in vitro. However, GITR is equivalently up-regulated on activated T cells and therefore is apparently no more selective as a marker for Treg cells than is CD25 (McHugh et al., 2002; Shimizu et al., 2002). Moreover, there are numerous reports that CD4+CD25− cell populations can suppress certain immune functions (Annacker et al., 2001; Apostolou et al., 2002; Curotto de Lafulle et al., 2001; Graca et al., 2002; Shimizu and Moriizumi, 2003; Stephens and Mason, 2000). Nonetheless, the finding that CD25$^{high}$LAG-3$^{high}$ cells exhibit the greatest suppressive activity suggests that antibodies against both of these cell surface molecules may be used coordinately to manipulate Treg activity.

Our data show that LAG-3 is required for the maximal suppressive activity of both natural and induced Treg cells. However, is it sufficient? Thus far, the only molecule shown to confer regulatory activity on activated T cells is Foxp3 (Fontenot et al., 2003; Hori et al., 2003). Importantly we have shown here that ectopic expression of LAG-3, but not a functionally defective mutant, on CD4+ T cells can also confer regulatory activity.

Another key question is whether Treg cells suppress the reactivity of CD4+ and CD8+ effector cells through direct T-T interactions or through DC intermediaries. The identification of Treg selective and functional expression of LAG-3, a MHC class II binding molecule, should provide a new handle on dissecting mechanisms and manipulating Treg function for diseases in which these cells play an important role.

Example 10

Experimental Procedures

Transgenic Mice

The C3-HA transgenic mice have been previously described (Adler et al., 2000; Adler et al., 1998). In short, the hemagglutinin (HA) gene derived from the influenza virus A/PR/8/34 (Mount Sinai strain) has been placed under the control of the rat C3(1) promoter. Two founder lines were established in the B 10.D2 genetic background. These two founder lines, C3-HA$^{high}$ and C3-HA$^{low}$, which contain 30-50 and 3 transgene copies respectively, express the C3-HA hybrid mRNA in the same set of non-lymphoid tissues including the lung and prostate. While the difference in total HA protein expression between C3-HA$^{high}$ and C3-HA$^{low}$ was not directly measured, in the lung and prostate, where the expression levels are highest, the difference is roughly 1000-fold as shown by bioassay of tissue extract induced hybridoma cytokine release.

The TCR transgenic mouse line 6.5, that expresses a TCR recognizing an I-E$^d$-restricted HA epitope ($^{110}$SFERFEIF-PKE$^{120}$; SEQ ID NO: 7) (generously provided by Dr. Harald von Boehmer, Harvard University, Boston, Mass.), was back-crossed 9 generations onto the B10.D2 genetic background. The other TCR transgenic mouse line Clone-4, that expresses a TCR recognizing a K$^d$-restricted HA epitope ($^{518}$IYSTVASSL$^{526}$; SEQ ID NO: 8) (generously provided by Dr. Linda Sherman, Scripps Research Institute, La Jolla, Calif.), was also back-crossed more than 9 generations onto the Thy 1.1/1.1 B10.D2 genetic background. Because no clonotypic antibody is available for Clone-4 TCR, Thy 1.1 was used as a surrogate marker. Following adoptive transfer into Thy1.2/1.2 recipients, we can assume that all the Thy 1.1$^+$ CD8$^+$ T cells express the HA-specific clonotypic TCR as nearly all of the mature CD8$^+$ T cells in the Clone-4 mice directly recognize the K$^d$-restricted HA epitope (Morgan et al., 1996).

Transgenic mice used for experiments were between the age of 8 to 24 weeks. All experiments involving the use of mice were performed in accordance with protocols approved by the Animal Care and Use Committee of the Johns Hopkins University School of Medicine.

Adoptive Transfer

Clonotypic CD4$^+$ or CD8$^+$ T cells were prepared from pooled spleens and lymph nodes of 6.5 or Clone-4 transgenic mice. Clonotypic percentage was determined by flow cytometry analysis. The activation marker CD44 was analyzed to ensure that these clonotypic cells were not activated in donor mice and were naive in phenotype. After washing 3 times with HBSS, an appropriate number of cells were resuspended in 0.2 ml of HBSS for i.v. injection through the tail vein.

Immunohistochemistry

Tissues were harvested from mice three days after adoptive transfer. Tissue was fixed in ImmunoHistoFix (A Phase sprl, Belgium) for 3 days at 4° C. and then embedded in Immuno-HistoWax (A Phase sprl, Belgium). Serial sections were stained using biotin-labeled anti-Thy1.1 mAb (PharMingen, San Diego, Calif.). The Vectastain ABC kit (Vector, Burlingame, Calif.) and NovaRed (Vector) were used for development. Sections were counterstained with hematoxylin QS (Vector). Sections were analyzed using a Nikon Eclipse E800. Final image processing was performed using Adobe PhotoShop (Mountain View, Calif.).

Enrichment and Purification of In Vivo Primed 6.5 CD4+ T Cells

With either effector/memory or tolerance induction in vivo after adoptive transfer, the clonotypic percentage of 6.5 CD4+ T cells in the spleens of recipient mice is only 0.2%~5%. Deliberate enrichment and purification is mandatory to obtain enough clonotypic CD4+ T cells for further studies, such as for Affymetrix gene chip analysis. Donor 6.5 T cells were crossed onto a Thy1.1(+)Thy1.2(−) background which allowed for a two step enrichment and purification procedure after adoptive transfer into Thy1.1(−)/Thy1.2(+) recipients. 6.5 CD4+ T cells were first enriched by using biotinylated anti-CD8 (Ly-2, 53-6.7), anti-B220 (RA3-6B2), and anti-Thy1.2 (30-H12) antibodies (all purchased from BD Biosciences PharMingen, San Diego, Calif.) and MACS streptavidin microbeads and MACS LS separation column (Miltenyi Biotech, Auburn, Calif.) to deplete CD8+ T cells, B cells and the recipient T cells (Thy 1.2+). Since CD4+ T cells and CD8+ T cells are the only populations bearing Thy1.1, and because CD8+ T cells had been depleted during enrichment, sorting for Thy1.1(+) cells using FACSVantage SE cell sorter (BD Biosciences) resulted in highly purified 6.5 CD4+ T cells (95%). This technique avoids the use of TCR-specific or CD4 coreceptor specific antibodies that could potentially alter TCR or CD4 dependent gene expression patterns.

Gene Chip Analysis

Sorted cells were sheared with Qiashredder columns (Qiagen, Valencia Calif.), followed by total RNA isolation using the RNeasy kit (Qiagen). cDNA was synthesized using the Superscript Choice kit (Gibco/BRL) and an HPLC purified T7-DT primer (Proligo, Boulder, Colo.). Biotinylated cRNA probe was prepared using the ENZO BioArray RNA transcript kit (Affymetrix, Santa Clara, Calif.). Murine gene chips U174A, B and C were hybridized and analyzed according to standard Affymetrix protocols.

Ranking the Differential Expression of Genes in CD4+ T Cells Between Anergy/Treg Induction and Effector/Memory Induction.

mRNA prepared from purified naïve 6.5 clonotypic CD4+ T cells and anergic/Treg and effector/memory 6.5 clonotypic CD4+ T cells on various days after adoptive transfer was analyzed by Affymetrix gene chips. The differential expression of genes between anergy/Treg induction and effector/memory induction was ranked by "distance". The distance was defined as the sum of the absolute differences of expression between anergic T cells and effector/memory T cells on day 2 (|d1|), day 3 (|d2|), and day 4 (|d3|) after adoptive transfer, divided by the value of naïve CD4+ T cells (n) for normalization.

Antibodies and Staining

The following antibodies were used. Anti-LAG-3 (C9B7W, from PharMingen) (Workman et al., 2002b) either purified or PE conjugated; anti-CD25 (7D4, from PharMingen) either purified or FITC conjugated; and anti-GITR (polyclonal antibody purchased from R&D Systems). For cell surface staining for LAG-3 and CD25, splenocytes from 6.5+/−Thy1.1+/− transgenic mice were isolated and enriched for CD4+ using a CD4+ negative selection isolation kit (Miltenyi Biotec). Approximately $2.5 \times 10^6$ clonotypic 6.5 cells, as determined by flow cytometry (16% of total CD4+ cells) were resuspended in HBSS and injected via tail vein into 137 (C3-HA high) or wild type B10.D2. One group of B10.D2 mice was treated with $5 \times 10^6$ Vac-HA, while the other group was left untreated for naïve control. Splenocytes and inguinal and axillary lymph nodes were harvested five days later and prepared into a single cell suspension. RBCs were lysed with ACK lysis buffer. Cells were immediately blocked with 5 ug whole rat IgG (Sigma) for 15 minutes before staining with anti-6.5 TCR-biotin+SA-APC, LAG-3-PE, and CD25-FITC, or the corresponding isotype controls. All staining reagents except anti-6.5-biotin were purchased from Pharmingen (San Diego, Calif.). After short incubation, samples were washed once in PBS+1% FBS solution and read on a FACScalibur machine (BD, San Jose, Calif.).

In vitro Suppression Assay for Induced 6.5 Regulatory T cells $1 \times 10^4$ purified naive 6.5 CD4+ T cells (Responders) and $1 \times 10^5$ 3000-rad irradiated syngeneic B10.D2 splenocytes (Antigen Presenting Cells) were mixed with different numbers of suppressor 6.5 CD4+ T cells and incubated in round bottom 96-well tissue culture plates with 10 µg/ml of HA class II ($^{110}$SFERFEIFPKE$^{120}$; SEQ NO: 7) peptide in 200 µl of CTL media. Forty-eight to 72 hours later, cultures were pulsed with 1 µCi $^3$H-thymidine and incubated an additional 16 hours before harvest with a Packard Micromate cell harvester. Determination of the amount of incorporated radioactive counts was performed with a Packard Matrix 96 direct beta counter (Packard Biosciences, Meriden, Conn.).

In Vitro Suppression Assay for Natural Regulatory T Cells

Wild type BALB/c mice were used for out natural Treg assays. $5 \times 10^4$ flow cytometry sorted CD4+CD25− T cells (Responders) and $5 \times 10^4$ 3000-rad irradiated BALB/c splenocytes (Antigen Presenting Cells) were mixed with different numbers of flow cytometry sorted CD4+CD25+ suppressor T cells and incubated in round bottom 96-well tissue culture plates with 0.5 µg/ml of anti-CD3 antibody in 200 µl of CTL media. Forty-eight to 72 hours later, cultures were pulsed with 1 µCi $^3$H-thymidine and incubated an additional 16 hours before harvest with a Packard Micromate cell harvester. Determination of the amount of incorporated radioactive counts was performed with a Packard Matrix 96 direct beta counter (Packard Biosciences, Meriden, Conn.).

Quantitative Real-Time PCR Analysis

The sorted 6.5 CD4+ T cells were immediately used for RNA extraction using Trizol reagent (Invitrogen, Carlsbad, Calif.). Reverse transcription was performed with the Superscript First Strand Synthesis System (Invitrogen, Carlsbad, Calif.). cDNA levels were analyzed by real-time quantitative PCR with the Taqman system (Applied Biosystems, Foster City, Calif.). Each sample was assayed in duplicates or triplicates for the target gene together with 18S rRNA as the internal reference in 25 µl final reaction volume, using the Taqman Universal PCR Master Mix and the ABI Prism 7700 Sequence Detection system. Pre-made reaction reagents (PDARs) were purchased from Applied Biosystems for detection of IL-10 and IL-2. Primer pair and probe sets were designed using Primer Express software and then synthesized by Applied Biosystems for LAG-3, CD25, GITR and IFN-γ. Primer and probe set used for Foxp3 was quoted from literature (S4). The relative mRNA frequencies were determined by normalization to the internal control 18S RNA. Briefly, we normalized each set of samples using the difference in the threshold cycles (Ct) between the target gene and the 18S RNA: $\Delta Ct_{sample}=(Ct_{sample}-Ct_{18S})$. The calibration sample was assigned as the sample with the highest ΔCt in each set of assay ($\Delta Ct_{calibration}$). Relative mRNA frequencies were calculated as $2^{\Delta\Delta Ct}$ where $\Delta\Delta Ct=(\Delta Ct_{calibration}-\Delta Ct_{sample})$. Primers and probe sets used are: LAG-3 Primer 5'-ACA TCA ACC AGA CAG TGG CCA-3'(SEQ ID NO: 9)/Primer 5'-GCA TCC CCT GGT GAA GGT C-3'(SEQ ID NO: 10)/Probe 5'-6FAM-CCC ACT CCC ATC CCG GCC C-TAMRA-3'(SEQ ID NO: 11); CD25 Primer 5'-TGT ATG ACC CAC CCG AGG TC-3'(SEQ ID NO: 12)/Primer 5'-TTA GGA TGG TGC CGT TCT TGT-3' (SEQ ID NO: 13)/Probe 5'-6FAM-CCA ATG CCA CAT TCA AAG CCC TCT CC-TAMRA-3'(SEQ ID NO: 14); GITR Primer 5'-TCC GGT GTG TTG CCT GTG-3'(SEQ ID NO: 15)/Primer 5'-CAA AGT CTG CAG TGA CCG TCA-3'(SEQ ID NO: 16)/Probe 5'-6FAM-CAT GGG CAC CTT CTC CGC AGG T-TAMRA-3'(SEQ ID NO: 17); IFN-γ Primer 5'-CAT TGA AAG CCT AGA AAG TCT GAA TAA C-3'(SEQ ID NO: 18)/Primer 5'-TGG CTC TGC AGG ATT TTC ATG-3'(SEQ ID NO: 19)/Probe 5'-6FAM-TCA CCA TCC TTT TGC CAG TTC CTC CAG-TAMRA-3'(SEQ ID NO: 20); Foxp3 Prime 5'-CCC AGG AAA GAC AGC AAC CTT-3'(SEQ ID NO: 21)/Primer 5'-TTC TCA CAA CCA GGC CAC TTG-3'(SEQ ID NO: 22)/Probe: 5'-6FAM-ATC CTA CCC ACT GCT GGC AAA TGG AGT C-3'(SEQ ID NO: 23).

LAG-3 Constructs and Retroviral Producer Cell Lines.

LAG-3 constructs were produced using recombinant PCR as described (Vignali and Vignali, 1999). The LAG-3.WT and the functionally null mutant LAG-3.Y73F.ΔCY (cytoplasmic tailless LAG-3 with a point mutation that greatly reduces the ability of LAG-3 to bind MHC class II) have been described (Workman et al., 2002a). LAG-3 constructs were cloned into a murine stem cell virus (MSCV)-based retroviral vector, which contained an internal ribosomal entry site (IRES) and green fluorescent protein (GFP), and retrovirus was produced as described (Persons et al., 1997; Persons et al., 1998). Retroviral producer cell lines were generated by repeatedly transducing GPE+86 cells (~7-10 times) until a viral titer of greater than $10^5$/ml after 24 h was obtained (Markowitz et al., 1988).

Retroviral Transduction of CD4+/CD25− T Cells and In Vitro Suppression Assay.

Splenocytes from 6.5 mice were stained with biotin labeled anti-B220, anti-Gr1, anti-Mac1, anti-TER119, anti-CD49b, anti-CD8 and anti-CD25 antibody (PharMingen, San Diego, Calif.). The cells were then incubated with magnetic beads coupled with streptavidin and negatively sorted on an autoMACS (Miltenyi Biotech, Auburn Calif.) to 90-95% purity of CD4$^+$/CD25$^-$ T cells. The purified 6.5 CD4$^+$/CD25$^-$ T cells were activated by plate bound anti-CD3 (2C11) and anti-CD28 (35.71). On days 2 and 3 post-stimulation, the activated T cells ($4\times10^5$ cells/ml) were spin transduced (90 min, 3000 rpm) with viral supernatant from vector alone, LAG-3.WT/GFP or LAG-3.Y73F.ΔCY/GFP retroviral GPE+ 86 producer cell lines described above plus IL-2 and polybrene (6 μg/ml). The cells were allowed to rest for 10 days and then sorted on the top ~30-35% GFP$^+$/Thy1.2$^+$ T cells.

For the in vitro suppression assay, the purified GFP$^+$ T cells were cultured (2 fold dilutions starting at $2.5\times10^4$) with $2.5\times10^4$ CD4$^+$/CD25$^-$ 6.5 T cells (purified by negative AutoMACS), $5\times10^4$ irradiated (3000 rads) splenocytes, and 5 μg/ml HA110-120 in a 96-well round bottom plate. The cells were cultured for 72 h and pulsed with [$^3$H]thymidine 1 μCi/well (Du Pont, Wilmington, Del.) the last 7-8 h of culture.

Example 11

CD223 is cleaved from the cell surface and released in a soluble form (sLAG-3). It is generated in significant amounts by activated T cells in vitro (5 μg/ml) and is also found in the serum of mice (80 ng/ml). It is likely generated by a cell surface protease. We detected sLAG-3 by Western blot. The cleavage occurs in the transmembrane region (e.g., amino acids 442-466 in SEQ ID NO: 2) or in the connector region (e.g., amino acids 432-441 in SEQ ID NO: 2) immediately preceding it amino-terminally.

Example 12

As shown above, LAG-3 is not only required for maximal regulatory T cells (Treg) function but is also sufficient. In other words, expression of LAG-3 alone is sufficient to convert cells from activated effector T cells into regulatory T cells.

We next wanted to determine if cells ectopically expressing LAG-3 would also exhibit regulatory function in vivo and be protected in a disease setting. We chose to ask whether ectopic expression of LAG-3 on an autoantigen-specific T cell could protect mice from type 1 diabetes. In this experimental system, splenocytes from diabetes-prone NOD mice were adoptively transferred to NOD-Scid mice, which lack lymphocytes. All mice develop diabetes within 3 months. Our preliminary analysis suggests that diabetes onset induced by NOD splenocytes is prevented by phogrin-specific T cells transduced with LAG-3, but not a signaling defective mutant or the GFP control. These data support the idea of using ectopic expression of autoantigen specific T cells with LAG-3 as a novel therapeutic for the treatment of many autoimmune diseases, asthma, and allergy.

REFERENCES

Adler, A. J., Huang, C. T., Yochum, G. S., Marsh, D. W., and Pardoll, D. M. (2000). In vivo CD4+ T cell tolerance induction versus priming is independent of the rate and number of cell divisions. J Immunol 164, 649-655.

Adler, A. J., Marsh, D. W., Yochum, G. S., Guzzo, J. L., Nigam, A., Nelson, W. G., and Pardoll, D. M. (1998). CD4+ T cell tolerance to parenchymal self-antigens requires presentation by bone marrow-derived antigen-presenting cells. J Exp Med 187, 1555-1564.

Almeida, A. R., Legrand, N., Papiernik, M., and Freitas, A. A. (2002). Homeostasis of peripheral CD4+ T cells: IL-2R alpha and IL-2 shape a population of regulatory cells that controls CD4+ T cell numbers. J Immunol 169, 4850-4860.

Annacker, O., Burlen-Defranoux, O., Pimenta-Araujo, R., Cumano, A., and Bandeira, A. (2000). Regulatory CD4 T cells control the size of the peripheral activated/memory CD4 T cell compartment. J Immunol 164, 3573-3580.

Annacker, O., Pimenta-Araujo, R., Burlen-Defranoux, O., Barbosa, T. C., Cumano, A., and Bandeira, A. (2001). CD25+ CD4+ T cells regulate the expansion of peripheral CD4 T cells through the production of IL-10. J Immunol 166, 3008-3018.

Apostolou, I., Sarukhan, A., Klein, L., and Von Boehmer, H. (2002). Origin of regulatory T cells with known specificity for antigen. Nat Immunol 3, 756-763.

Belkaid, Y., Piccirillo, C. A., Mendez, S., Shevach, E. M., and Sacks, D. L. (2002). CD4+CD25+ regulatory T cells control *Leishmania major* persistence and immunity. Nature 420, 502-507.

Curotto de Lafulle, M. A., and Lafulle, J. J. (2002). CD4(+) regulatory T cells in autoimmunity and allergy. Curr Opin Immunol 14, 771-778.

Curotto de Lafulle, M. A., Muriglan, S., Sunshine, M. J., Lei, Y., Kutchukhidze, N., Furtado, G. C., Wensky, A. K., Olivares-Villagomez, D., and Lafulle, J. J. (2001). Hyper immunoglobulin E response in mice with monoclonal populations of B and T lymphocytes. J Exp Med 194, 1349-1359.

Fontenot, J. D., Gavin, M. A., and Rudensky, A. Y. (2003). Foxp3 programs the development and function of CD4+ CD25+ regulatory T cells. Nat Immunol 4, 330-336.

Graca, L., Thompson, S., Lin, C. Y., Adams, E., Cobbold, S. P., and Waldmann, H. (2002). Both CD4(+)CD25(+) and CD4(+)CD25(−) regulatory cells mediate dominant transplantation tolerance. J Immunol 168, 5558-5565.

Hannier, S., Tournier, M., Bismuth, G., and Triebel, F. (1998). CD3/TCR complex-associated lymphocyte activation gene-3 molecules inhibit CD3/TCR signaling. J Immunol 161, 4058-4065.

Hori, S., Nomura, T., and Sakaguchi, S. (2003). Control of regulatory T cell development by the transcription factor Foxp3. Science 299, 1057-1061.

Huang, C.-T., Huso, D. L., Lu, Z., Wang, T., Zhou, G., Kennedy, E. P., Drake, C. G., Morgan, D. J., Sherman, L. A., Higgins, A. D., et al. (2003). CD4+ T Cells Pass Through an Effector Phase During the Process of In Vivo Tolerance Induction. J Immunol 170, 3945-3953.

Huard, B., Tournier, M., Hercend, T., Triebel, F., and Faure, F. (1994). Lymphocyte-activation gene 3/major histocompatibility complex class II interaction modulates the antigenic response of CD4+ T lymphocytes. Eur J Immunol 24, 3216-3221.

Jonuleit, H., and Schmitt, E. (2003). The regulatory T cell family: distinct subsets and their interrelations. J Immunol 171, 6323-6327.

Jooss, K., Gjata, B., Danos, 0., von Boehmer, H., and Sarukhan, A. (2001). Regulatory function of in vivo anergized CD4(+) T cells. Proc Natl Acad Sci USA 98, 8738-8743.

Khattri, R., Cox, T., Yasayko, S. A., and Ramsdell, F. (2003). An essential role for Scurfin in CD4+CD25+T regulatory cells. Nat Immunol 4, 337-342.

Maloy, K. J., and Powrie, F. (2001). Regulatory T cells in the control of immune pathology. Nat Immunol 2, 816-822.

Markowitz, D., Goff, S., and Bank, A. (1988). A safe packaging line for gene transfer: separating viral genes on two different plasmids. J Virol 62, 1120-1124.

McHugh, R. S., Whitters, M. J., Piccirillo, C. A., Young, D. A., Shevach, E. M., Collins, M., and Byrne, M. C. (2002). CD4(+)CD25(+) immunoregulatory T cells: gene expression analysis reveals a functional role for the glucocorticoid-induced TNF receptor. Immunity 16, 311-323.

Miyazaki, T., Dierich, A., Benoist, C., and Mathis, D. (1996). Independent modes of natural killing distinguished in mice lacking Lag3. Science 272, 405-408.

Moore, K. W., de Waal Malefyt, R., Coffman, R. L., and O'Garra, A. (2001). Interleukin-10 and the interleukin-10 receptor. Annu Rev Immunol 19, 683-765.

Morgan, D. J., Liblau, R., Scott, B., Fleck, S., McDevitt, H. O., Sarvetnick, N., Lo, D., and Sherman, L. A. (1996). CD8(+) T cell-mediated spontaneous diabetes in neonatal mice. J Immunol 157, 978-983.

Nishimura, H., Nose, M., Hiai, H., Minato, N., and Honjo, T. (1999). Development of lupus-like autoimmune diseases by disruption of the PD-1 gene encoding an ITIM motif-carrying immunoreceptor. Immunity 11, 141-151.

Nishimura, H., Okazaki, T., Tanaka, Y., Nakatani, K., Hara, M., Matsumori, A., Sasayama, S., Mizoguchi, A., Hiai, H., Minato, N., and Honjo, T. (2001). Autoimmune dilated cardiomyopathy in PD-1 receptor-deficient mice. Science 291, 319-322.

Persons, D. A., Allay, J. A., Allay, E. R., Smeyne, R. J., Ashmun, R. A., Sorrentino, B. P., and Nienhuis, A. W. (1997). Retroviral-mediated transfer of the green fluorescent protein gene into murine hematopoietic cells facilitates scoring and selection of transduced progenitors in vitro and identification of genetically modified cells in vivo. Blood 90, 1777-1786.

Persons, D. A., Mehaffey, M. G., Kaleko, M., Nienhuis, A. W., and Vanin, E. F. (1998). An improved method for generating retroviral producer clones for vectors lacking a selectable marker gene. Blood Cells Mol Dis 24, 167-182.

Read, S., Malmstrom, V., and Powrie, F. (2000). Cytotoxic T lymphocyte-associated antigen 4 plays an essential role in the function of CD25(+)CD4(+) regulatory cells that control intestinal inflammation. J Exp Med 192, 295-302.

Sakaguchi, S., Sakaguchi, N., Shimizu, J., Yamazaki, S., Sakihama, T., Itoh, M., Kuniyasu, Y., Nomura, T., Toda, M., and Takahashi, T. (2001). Immunologic tolerance maintained by CD25+ CD4+ regulatory T cells: their common role in controlling autoimmunity, tumor immunity, and transplantation tolerance. Immunol Rev 182, 18-32.

Shevach, E. M. (2002). CD4+ CD25+ suppressor T cells: more questions than answers. Nat Rev Immunol 2, 389-400.

Shimizu, J., and Moriizumi, E. (2003). CD4+CD25− T Cells in Aged Mice Are Hyporesponsive and Exhibit Suppressive Activity J Immunol 170, 1675-1682.

Shimizu, J., Yamazaki, S., Takahashi, T., Ishida, Y., and Sakaguchi, S. (2002). Stimulation of CD25(+)CD4(+) regulatory T cells through GITR breaks immunological self-tolerance. Nat Immunol 3, 135-142.

Stephens, L. A., and Mason, D. (2000). CD25 is a marker for CD4+ thymocytes that prevent autoimmune diabetes in rats, but peripheral T cells with this function are found in both CD25+ and CD25− subpopulations. J Immunol 165, 3105-3110.

Sutmuller, R. P., van Duivenvoorde, L. M., van Elsas, A., Schumacher, T. N., Wildenberg, M. E., Allison, J. P., Toes, R. E., Offring a, R., and Melief, C. J. (2001). Synergism of cytotoxic T lymphocyte-associated antigen 4 blockade and depletion of CD25(+) regulatory T cells in antitumor therapy reveals alternative pathways for suppression of autoreactive cytotoxic T lymphocyte responses. J Exp Med 194, 823-832.

Suvas, S., Kumaraguru, U., Pack, C. D., Lee, S., and Rouse, B. T. (2003). CD4+CD25+ T Cells Regulate Virus-specific Primary and Memory CD8+ T Cell Responses. J Exp Med 198, 889-901.

Vignali, D. A., and Vignali, K. M. (1999). Profound enhancement of T cell activation mediated by the interaction between the TCR and the D3 domain of CD4. J Immunol 162, 1431-1439.

von Boehmer, H. (2003). Dynamics of Suppressor T Cells: In Vivo Veritas. J Exp Med 198, 845-849.

Workman, C. J., Dugger, K. J., and Vignali, D. A. A. (2002a). Cutting Edge: Molecular Analysis of the Negative Regulatory Function of Lymphocyte Activation Gene-3. J Immunol 169, 5392-5395.

Workman, C. J., Rice, D. S., Dugger, K. J., Kurschner, C., and Vignali, D. A. (2002b). Phenotypic analysis of the murine CD4-related glycoprotein, CD223 (LAG-3). Eur J Immunol 32, 2255-2263.

The invention claimed is:

1. A composition, comprising:
antibodies which specifically bind to and inhibit negative T cell regulatory function of CD223; and
an anti-cancer vaccine.

2. The composition of claim 1 which is a pharmaceutical composition.

3. The composition of claim 1 wherein the antibodies are monoclonal antibodies.

4. A kit comprising:
antibodies which specifically bind to and inhibit negative T cell regulatory function of CD223; and
an anti-cancer vaccine.

5. The kit of claim 4 wherein said antibodies and vaccine are in separate containers.

6. The kit of claim 4 further comprising instructions for administration of components of the kit to a cancer patient.

* * * * *

UNITED STATES PATENT AND TRADEMARK OFFICE
CERTIFICATE OF CORRECTION

| | |
|---|---|
| PATENT NO. | : 8,551,481 B2 |
| APPLICATION NO. | : 12/578887 |
| DATED | : October 8, 2013 |
| INVENTOR(S) | : Pardoll et al. |

It is certified that error appears in the above-identified patent and that said Letters Patent is hereby corrected as shown below:

In the Specification

After the title, line 5, replace the first paragraph as follows:

STATEMENT OF GOVERNMENTAL INTEREST

This invention was made with government support under grant no. AI039480, awarded by the National Institutes of Health. The government has certain rights in the invention.

Signed and Sealed this
Seventeenth Day of March, 2015

Michelle K. Lee
*Director of the United States Patent and Trademark Office*

SEQUENCE LISTING

<160> NUMBER OF SEQ ID NOS: 23

<210> SEQ ID NO 1
<211> LENGTH: 1566
<212> TYPE: DNA
<213> ORGANISM: Mus musculus
<220> FEATURE:
<221> NAME/KEY: misc_feature
<222> LOCATION: (1)...(1566)
<223> OTHER INFORMATION: murine LAG-3
<220> FEATURE:
<221> NAME/KEY: CDS
<222> LOCATION: (1)...(1566)
<223> OTHER INFORMATION: murine LAG-3 protein
<220> FEATURE:
<221> NAME/KEY: sig_peptide
<222> LOCATION: (1)...(66)

<400> SEQUENCE: 1

```
atg agg gag gac ctg ctc ctt ggc ttt ttg ctt ctg gga ctg ctt tgg      48
Met Arg Glu Asp Leu Leu Leu Gly Phe Leu Leu Leu Gly Leu Leu Trp
        -20              -15              -10 gaa gct cca gtt gtg tct tca ggg cct ggg aaa gag ctc ccc gtg gtg      96
Glu Ala Pro Val Val Ser Ser Gly Pro Gly Lys Glu Leu Pro Val Val
    -5                1                5                10 tgg gcc cag gag gga gct ccc gtc cat ctt ccc tgc agc ctc aaa tcc     144
Trp Ala Gln Glu Gly Ala Pro Val His Leu Pro Cys Ser Leu Lys Ser
                15              20              25 ccc aac ctg gat cct aac ttt cta cga aga ggg ggg gtt atc tgg caa     192
Pro Asn Leu Asp Pro Asn Phe Leu Arg Arg Gly Gly Val Ile Trp Gln
            30              35              40 cat caa cca gac agt ggc caa ccc act ccc atc ccg gcc ctt gac ctt     240
His Gln Pro Asp Ser Gly Gln Pro Thr Pro Ile Pro Ala Leu Asp Leu
        45              50              55 cac cag ggg atg ccc tcg cct aga caa ccc gca ccc ggt cgc tac acg     288
His Gln Gly Met Pro Ser Pro Arg Gln Pro Ala Pro Gly Arg Tyr Thr
    60                  65              70 gtg ctg agc gtg gct cca gga ggc ctg cgc agc ggg agg cag ccc ctg     336
Val Leu Ser Val Ala Pro Gly Gly Leu Arg Ser Gly Arg Gln Pro Leu
75              80              85                  90 cat ccc cac gtg cag ctg gag gag cgc ggc ctc cag cgc ggg gac ttc     384
His Pro His Val Gln Leu Glu Glu Arg Gly Leu Gln Arg Gly Asp Phe
                95              100             105 tct ctg tgg ttg cgc cca gct ctg cgc acc gat gcg ggc gag tac cac     432
Ser Leu Trp Leu Arg Pro Ala Leu Arg Thr Asp Ala Gly Glu Tyr His
            110             115             120 gcc acc gtg cgc ctc ccg aac cgc gcc ctc tcc tgc agt ctc cgc ctg     480
Ala Thr Val Arg Leu Pro Asn Arg Ala Leu Ser Cys Ser Leu Arg Leu
        125             130             135 cgc gtc ggc cag gcc tcg atg att gct agt ccc tca gga gtc ctc aag     528
Arg Val Gly Gln Ala Ser Met Ile Ala Ser Pro Ser Gly Val Leu Lys
    140             145             150 ctg tct gat tgg gtc ctt ttg aac tgc tcc ttc agc cgt cct gac cgc     576
Leu Ser Asp Trp Val Leu Leu Asn Cys Ser Phe Ser Arg Pro Asp Arg
155             160             165             170 cca gtc tct gtg cac tgg ttc cag ggc cag aac cga gtg cct gtc tac     624
Pro Val Ser Val His Trp Phe Gln Gly Gln Asn Arg Val Pro Val Tyr
                175             180             185
```

```
aac tca ccg cgt cat ttt tta gct gaa act ttc ctg tta ctg ccc caa    672
Asn Ser Pro Arg His Phe Leu Ala Glu Thr Phe Leu Leu Leu Pro Gln
        190                 195                 200 gtc agc ccc ctg gac tct ggg acc tgg ggc tgt gtc ctc acc tac aga    720
Val Ser Pro Leu Asp Ser Gly Thr Trp Gly Cys Val Leu Thr Tyr Arg
            205                 210                 215 gat ggc ttc aat gtc tcc atc acg tac aac ctc aag gtt ctg ggt ctg    768
Asp Gly Phe Asn Val Ser Ile Thr Tyr Asn Leu Lys Val Leu Gly Leu
    220                 225                 230 gag ccc gta gcc cct ctg aca gtg tac gct gct gaa ggt tct agg gtg    816
Glu Pro Val Ala Pro Leu Thr Val Tyr Ala Ala Glu Gly Ser Arg Val
235                 240                 245                 250 gag ctg ccc tgt cat ttg ccc cca gga gtg ggg acc cct tct ttg ctc    864
Glu Leu Pro Cys His Leu Pro Pro Gly Val Gly Thr Pro Ser Leu Leu
                255                 260                 265 att gcc aag tgg act cct cct gga gga ggt cct gag ctc ccc gtg gct    912
Ile Ala Lys Trp Thr Pro Pro Gly Gly Gly Pro Glu Leu Pro Val Ala
            270                 275                 280 gga aag agt ggc aat ttt acc ctt cac ctt gag gct gtg ggt ctg gca    960
Gly Lys Ser Gly Asn Phe Thr Leu His Leu Glu Ala Val Gly Leu Ala
    285                 290                 295 cag gct ggg acc tac acc tgt agc atc cat ctg cag gga cag cag ctc   1008
Gln Ala Gly Thr Tyr Thr Cys Ser Ile His Leu Gln Gly Gln Gln Leu
300                 305                 310 aat gcc act gtc acg ttg gcg gtc atc aca gtg act ccc aaa tcc ttc   1056
Asn Ala Thr Val Thr Leu Ala Val Ile Thr Val Thr Pro Lys Ser Phe
315                 320                 325                 330 ggg tta cct ggc tcc cgg ggg aag ctg ttg tgt gag gta acc ccg gca   1104
Gly Leu Pro Gly Ser Arg Gly Lys Leu Leu Cys Glu Val Thr Pro Ala
            335                 340                 345 tct gga aag gaa aga ttt gtg tgg cgt ccc ctg aac aat ctg tcc agg   1152
Ser Gly Lys Glu Arg Phe Val Trp Arg Pro Leu Asn Asn Leu Ser Arg
    350                 355                 360 agt tgc ccg ggc cct gtg ctg gag att cag gag gcc agg ctc ctt gct   1200
Ser Cys Pro Gly Pro Val Leu Glu Ile Gln Glu Ala Arg Leu Leu Ala
365                 370                 375 gag cga tgg cag tgt cag ctg tac gag ggc cag agg ctt ctt gga gcg   1248
Glu Arg Trp Gln Cys Gln Leu Tyr Glu Gly Gln Arg Leu Leu Gly Ala
380                 385                 390 aca gtg tac gcc gca gag tct agc tca ggc gcc cac agt gct agg aga   1296
Thr Val Tyr Ala Ala Glu Ser Ser Ser Gly Ala His Ser Ala Arg Arg
395                 400                 405                 410 atc tca ggt gac ctt aaa gga ggc cat ctc gtt ctc gtt ctc atc ctt   1344
Ile Ser Gly Asp Leu Lys Gly Gly His Leu Val Leu Val Leu Ile Leu
            415                 420                 425 ggt gcc ctc tcc ctg ttc ctt ttg gtg gcc ggg gcc ttt ggc ttt cac   1392
Gly Ala Leu Ser Leu Phe Leu Leu Val Ala Gly Ala Phe Gly Phe His
    430                 435                 440 tgg tgg aga aaa cag ttg cta ctg aga aga ttt tct gcc tta gaa cat   1440
Trp Trp Arg Lys Gln Leu Leu Leu Arg Arg Phe Ser Ala Leu Glu His
        445                 450                 455 ggg att cag cca ttt ccg gct cag agg aag ata gag gag ctg gag cga   1488
Gly Ile Gln Pro Phe Pro Ala Gln Arg Lys Ile Glu Glu Leu Glu Arg
    460                 465                 470 gaa ctg gag acg gag atg gga cag gag ccg gag ccc gag ccg gag cca   1536
Glu Leu Glu Thr Glu Met Gly Gln Glu Pro Glu Pro Glu Pro Glu Pro
475                 480                 485                 490 cag ctg gag cca gag ccc agg cag ctc tga                           1566
Gln Leu Glu Pro Glu Pro Arg Gln Leu  *
            495
```

```
<210> SEQ ID NO 2
<211> LENGTH: 521
<212> TYPE: PRT
<213> ORGANISM: Mus musculus
<220> FEATURE:
<221> NAME/KEY: SIGNAL
<222> LOCATION: (1)...(22)
<223> OTHER INFORMATION: leader sequence
<220> FEATURE:
<221> NAME/KEY: TRANSMEM
<222> LOCATION: (442)...(466)
<220> FEATURE:
<221> NAME/KEY: DOMAIN
<222> LOCATION: (432)...(441)
<223> OTHER INFORMATION: connecting
<220> FEATURE:
<221> NAME/KEY: DOMAIN
<222> LOCATION: (467)...(521)
<223> OTHER INFORMATION: cytoplasmic tail

<400> SEQUENCE: 2
```

Met Arg Glu Asp Leu Leu Gly Phe Leu Leu Gly Leu Trp
 1               5                  10                  15

Glu Ala Pro Val Val Ser Ser Gly Pro Gly Lys Glu Leu Pro Val Val
                20                  25                  30

Trp Ala Gln Glu Gly Ala Pro Val His Leu Pro Cys Ser Leu Lys Ser
            35                  40                  45

Pro Asn Leu Asp Pro Asn Phe Leu Arg Arg Gly Gly Val Ile Trp Gln
        50                  55                  60

His Gln Pro Asp Ser Gly Gln Pro Thr Pro Ile Pro Ala Leu Asp Leu
    65                  70                  75                  80

His Gln Gly Met Pro Ser Pro Arg Gln Pro Ala Pro Gly Arg Tyr Thr
                85                  90                  95

Val Leu Ser Val Ala Pro Gly Gly Leu Arg Ser Gly Arg Gln Pro Leu
            100                 105                 110

His Pro His Val Gln Leu Glu Glu Arg Gly Leu Gln Arg Gly Asp Phe
        115                 120                 125

Ser Leu Trp Leu Arg Pro Ala Leu Arg Thr Asp Ala Gly Glu Tyr His
    130                 135                 140

Ala Thr Val Arg Leu Pro Asn Arg Ala Leu Ser Cys Ser Leu Arg Leu
145                 150                 155                 160

Arg Val Gly Gln Ala Ser Met Ile Ala Ser Pro Ser Gly Val Leu Lys
                165                 170                 175

Leu Ser Asp Trp Val Leu Leu Asn Cys Ser Phe Ser Arg Pro Asp Arg
            180                 185                 190

Pro Val Ser Val His Trp Phe Gln Gly Gln Asn Arg Val Pro Val Tyr
        195                 200                 205

Asn Ser Pro Arg His Phe Leu Ala Glu Thr Phe Leu Leu Leu Pro Gln
    210                 215                 220

Val Ser Pro Leu Asp Ser Gly Thr Trp Gly Cys Val Leu Thr Tyr Arg
225                 230                 235                 240

Asp Gly Phe Asn Val Ser Ile Thr Tyr Asn Leu Lys Val Leu Gly Leu
                245                 250                 255

Glu Pro Val Ala Pro Leu Thr Val Tyr Ala Ala Glu Gly Ser Arg Val
            260                 265                 270

Glu Leu Pro Cys His Leu Pro Pro Gly Val Gly Thr Pro Ser Leu Leu
        275                 280                 285

Ile Ala Lys Trp Thr Pro Pro Gly Gly Gly Pro Glu Leu Pro Val Ala
    290                 295                 300

-continued

```
Gly Lys Ser Gly Asn Phe Thr Leu His Leu Glu Ala Val Gly Leu Ala
305                 310                 315                 320

Gln Ala Gly Thr Tyr Thr Cys Ser Ile His Leu Gln Gly Gln Gln Leu
            325                 330                 335

Asn Ala Thr Val Thr Leu Ala Val Ile Thr Val Thr Pro Lys Ser Phe
        340                 345                 350

Gly Leu Pro Gly Ser Arg Gly Lys Leu Leu Cys Glu Val Thr Pro Ala
    355                 360                 365

Ser Gly Lys Glu Arg Phe Val Trp Arg Pro Leu Asn Asn Leu Ser Arg
370                 375                 380

Ser Cys Pro Gly Pro Val Leu Glu Ile Gln Glu Ala Arg Leu Leu Ala
385                 390                 395                 400

Glu Arg Trp Gln Cys Gln Leu Tyr Glu Gly Gln Arg Leu Leu Gly Ala
                405                 410                 415

Thr Val Tyr Ala Ala Glu Ser Ser Gly Ala His Ser Ala Arg Arg
            420                 425                 430

Ile Ser Gly Asp Leu Lys Gly His Leu Val Leu Val Leu Ile Leu
    435                 440                 445

Gly Ala Leu Ser Leu Phe Leu Leu Val Ala Gly Ala Phe Gly Phe His
    450                 455                 460

Trp Trp Arg Lys Gln Leu Leu Leu Arg Arg Phe Ser Ala Leu Glu His
465                 470                 475                 480

Gly Ile Gln Pro Phe Pro Ala Gln Arg Lys Ile Glu Leu Glu Arg
                485                 490                 495

Glu Leu Glu Thr Glu Met Gly Gln Glu Pro Glu Pro Glu Pro Glu Pro
            500                 505                 510

Gln Leu Glu Pro Glu Pro Arg Gln Leu
        515                 520

<210> SEQ ID NO 3
<211> LENGTH: 1578
<212> TYPE: DNA
<213> ORGANISM: Homo sapiens
<220> FEATURE:
<221> NAME/KEY: CDS
<222> LOCATION: (1)...(1578)
<223> OTHER INFORMATION: human LAG-3
<220> FEATURE:
<221> NAME/KEY: sig_peptide
<222> LOCATION: (1)...(66)

<400> SEQUENCE: 3 atg tgg gag gct cag ttc ctg ggc ttg ctg ttt ctg cag ccg ctt tgg     48
Met Trp Glu Ala Gln Phe Leu Gly Leu Leu Phe Leu Gln Pro Leu Trp
            -20                 -15                 -10 gtg gct cca gtg aag cct ctc cag cca ggg gct gag gtc ccg gtg gtg     96
Val Ala Pro Val Lys Pro Leu Gln Pro Gly Ala Glu Val Pro Val Val
        -5                  1               5                  10 tgg gcc cag gag ggg gct cct gcc cag ctc ccc tgc agc ccc aca atc    144
Trp Ala Gln Glu Gly Ala Pro Ala Gln Leu Pro Cys Ser Pro Thr Ile
                15                  20                  25 ccc ctc cag gat ctc agc ctt ctg cga aga gca ggg gtc act tgg cag    192
Pro Leu Gln Asp Leu Ser Leu Leu Arg Arg Ala Gly Val Thr Trp Gln
            30                  35                  40 cat cag cca gac agt ggc ccg ccc gct gcc gcc ccc ggc cat ccc ctg    240
His Gln Pro Asp Ser Gly Pro Pro Ala Ala Ala Pro Gly His Pro Leu
        45                  50                  55 gcc ccc ggc cct cac ccg gcg gcg ccc tcc tcc tgg ggg ccc agg ccc    288
Ala Pro Gly Pro His Pro Ala Ala Pro Ser Ser Trp Gly Pro Arg Pro
    60                  65                  70
```

| | | |
|---|---|---|
| cgc cgc tac acg gtg ctg agc gtg ggt ccc gga ggc ctg cgc agc ggg<br>Arg Arg Tyr Thr Val Leu Ser Val Gly Pro Gly Gly Leu Arg Ser Gly<br>75                              80                        85                       90 | 336 |
| agg ctg ccc ctg cag ccc cgt gtc cag ctg gat gag cgc ggc cgg cag<br>Arg Leu Pro Leu Gln Pro Arg Val Gln Leu Asp Glu Arg Gly Arg Gln<br>95                         100                      105 | 384 |
| cgc ggg gac ttc tcg cta tgg ctg cgc cca gcc cgg cgc gcg gac gcc<br>Arg Gly Asp Phe Ser Leu Trp Leu Arg Pro Ala Arg Arg Ala Asp Ala<br>110                    115                      120 | 432 |
| ggc gag tac cgc gcc gcg gtg cac ctc agg gac cgc gcc ctc tcc tgc<br>Gly Glu Tyr Arg Ala Ala Val His Leu Arg Asp Arg Ala Leu Ser Cys<br>125                    130                      135 | 480 |
| cgc ctc cgt ctg cgc ctg ggc cag gcc tcg atg act gcc agc ccc cca<br>Arg Leu Arg Leu Arg Leu Gly Gln Ala Ser Met Thr Ala Ser Pro Pro<br>140                      145                      150 | 528 |
| gga tct ctc aga gcc tcc gac tgg gtc att ttg aac tgc tcc ttc agc<br>Gly Ser Leu Arg Ala Ser Asp Trp Val Ile Leu Asn Cys Ser Phe Ser<br>155                    160                      165                      170 | 576 |
| cgc cct gac cgc cca gcc tct gtg cat tgg ttc cgg aac cgg ggc cag<br>Arg Pro Asp Arg Pro Ala Ser Val His Trp Phe Arg Asn Arg Gly Gln<br>175                    180                      185 | 624 |
| ggc cga gtc cct gtc cgg gag tcc ccc cat cac cac tta gcg gaa agc<br>Gly Arg Val Pro Val Arg Glu Ser Pro His His His Leu Ala Glu Ser<br>190                    195                      200 | 672 |
| ttc ctc ttc ctg ccc caa gtc agc ccc atg gac tct ggg ccc tgg ggc<br>Phe Leu Phe Leu Pro Gln Val Ser Pro Met Asp Ser Gly Pro Trp Gly<br>205                    210                      215 | 720 |
| tgc atc ctc acc tac aga gat ggc ttc aac gtc tcc atc atg tat aac<br>Cys Ile Leu Thr Tyr Arg Asp Gly Phe Asn Val Ser Ile Met Tyr Asn<br>220                    225                      230 | 768 |
| ctc act gtt ctg ggt ctg gag ccc cca act ccc ttg aca gtg tac gct<br>Leu Thr Val Leu Gly Leu Glu Pro Pro Thr Pro Leu Thr Val Tyr Ala<br>235                    240                      245                      250 | 816 |
| gga gca ggt tcc agg gtg ggg ctg ccc tgc cgc ctg cct gct ggt gtg<br>Gly Ala Gly Ser Arg Val Gly Leu Pro Cys Arg Leu Pro Ala Gly Val<br>255                    260                      265 | 864 |
| ggg acc cgg tct ttc ctc act gcc aag tgg act cct cct ggg gga ggc<br>Gly Thr Arg Ser Phe Leu Thr Ala Lys Trp Thr Pro Pro Gly Gly Gly<br>270                    275                      280 | 912 |
| cct gac ctc ctg gtg act gga gac aat ggc gac ttt acc ctt cga cta<br>Pro Asp Leu Leu Val Thr Gly Asp Asn Gly Asp Phe Thr Leu Arg Leu<br>285                    290                      295 | 960 |
| gag gat gtg agc cag gcc cag gct ggg acc tac acc tgc cat atc cat<br>Glu Asp Val Ser Gln Ala Gln Ala Gly Thr Tyr Thr Cys His Ile His<br>300                    305                      310 | 1008 |
| ctg cag gaa cag cag ctc aat gcc act gtc aca ttg gca atc atc aca<br>Leu Gln Glu Gln Gln Leu Asn Ala Thr Val Thr Leu Ala Ile Ile Thr<br>315                    320                      325                      330 | 1056 |
| gtg act ccc aaa tcc ttt ggg tca cct gga tcc ctg ggg aag ctg ctt<br>Val Thr Pro Lys Ser Phe Gly Ser Pro Gly Ser Leu Gly Lys Leu Leu<br>335                    340                      345 | 1104 |
| tgt gag gtg act cca gta tct gga caa gaa cgc ttt gtg tgg agc tct<br>Cys Glu Val Thr Pro Val Ser Gly Gln Glu Arg Phe Val Trp Ser Ser<br>350                    355                      360 | 1152 |
| ctg gac acc cca tcc cag agg agt ttc tca gga cct tgg ctg gag gca<br>Leu Asp Thr Pro Ser Gln Arg Ser Phe Ser Gly Pro Trp Leu Glu Ala<br>365                    370                      375 | 1200 |
| cag gag gcc cag ctc ctt tcc cag cct tgg caa tgc cag ctg tac cag<br>Gln Glu Ala Gln Leu Leu Ser Gln Pro Trp Gln Cys Gln Leu Tyr Gln<br>380                    385                      390 | 1248 |

```
ggg gag agg ctt ctt gga gca gca gtg tac ttc aca gag ctg tct agc      1296
Gly Glu Arg Leu Leu Gly Ala Ala Val Tyr Phe Thr Glu Leu Ser Ser
395                 400                 405                 410 cca ggt gcc caa cgc tct ggg aga gcc cca ggt gcc ctc cca gca ggc      1344
Pro Gly Ala Gln Arg Ser Gly Arg Ala Pro Gly Ala Leu Pro Ala Gly
            415                 420                 425 cac ctc ctg ctg ttt ctc acc ctt ggt gtc ctt tct ctg ctc ctt ttg      1392
His Leu Leu Leu Phe Leu Thr Leu Gly Val Leu Ser Leu Leu Leu Leu
430                 435                 440 gtg act gga gcc ttt ggc ttt cac ctt tgg aga aga cag tgg cga cca      1440
Val Thr Gly Ala Phe Gly Phe His Leu Trp Arg Arg Gln Trp Arg Pro
            445                 450                 455 aga cga ttt tct gcc tta gag caa ggg att cac cct ccg cag gct cag      1488
Arg Arg Phe Ser Ala Leu Glu Gln Gly Ile His Pro Pro Gln Ala Gln
460                 465                 470 agc aag ata gag gag ctg gag caa gaa ccg gag ccg gag ccg gag ccg      1536
Ser Lys Ile Glu Glu Leu Glu Gln Glu Pro Glu Pro Glu Pro Glu Pro
475                 480                 485                 490 gaa ccg gag ccc gag ccc gag ccc gag ccg gag cag ctc tga              1578
Glu Pro Glu Pro Glu Pro Glu Pro Glu Pro Glu Gln Leu  *
            495                 500

<210> SEQ ID NO 4
<211> LENGTH: 525
<212> TYPE: PRT
<213> ORGANISM: Homo sapiens
<220> FEATURE:
<221> NAME/KEY: SIGNAL
<222> LOCATION: (1)...(22)
<220> FEATURE:
<221> NAME/KEY: TRANSMEM
<222> LOCATION: (450)...(474)
<220> FEATURE:
<221> NAME/KEY: DOMAIN
<222> LOCATION: (475)...(525)
<223> OTHER INFORMATION: CYTOPLASMIC TAIL
<220> FEATURE:
<221> NAME/KEY: DOMAIN
<222> LOCATION: (465)...(474)
<223> OTHER INFORMATION: CONNECTING PEPTIDE

<400> SEQUENCE: 4

Met Trp Glu Ala Gln Phe Leu Gly Leu Leu Phe Leu Gln Pro Leu Trp
1               5                   10                  15

Val Ala Pro Val Lys Pro Leu Gln Pro Gly Ala Glu Val Pro Val Val
            20                  25                  30

Trp Ala Gln Glu Gly Ala Pro Ala Gln Leu Pro Cys Ser Pro Thr Ile
        35                  40                  45

Pro Leu Gln Asp Leu Ser Leu Leu Arg Arg Ala Gly Val Thr Trp Gln
    50                  55                  60

His Gln Pro Asp Ser Gly Pro Pro Ala Ala Ala Pro Gly His Pro Leu
65                  70                  75                  80

Ala Pro Gly Pro His Pro Ala Ala Pro Ser Ser Trp Gly Pro Arg Pro
                85                  90                  95

Arg Arg Tyr Thr Val Leu Ser Val Gly Pro Gly Gly Leu Arg Ser Gly
            100                 105                 110

Arg Leu Pro Leu Gln Pro Arg Val Gln Leu Asp Glu Arg Gly Arg Gln
        115                 120                 125

Arg Gly Asp Phe Ser Leu Trp Leu Arg Pro Ala Arg Arg Ala Asp Ala
    130                 135                 140

Gly Glu Tyr Arg Ala Ala Val His Leu Arg Asp Arg Ala Leu Ser Cys
145                 150                 155                 160
```

-continued

```
Arg Leu Arg Leu Arg Leu Gly Gln Ala Ser Met Thr Ala Ser Pro Pro
                165                 170                 175
Gly Ser Leu Arg Ala Ser Asp Trp Val Ile Leu Asn Cys Ser Phe Ser
            180                 185                 190
Arg Pro Asp Arg Pro Ala Ser Val His Trp Phe Arg Asn Arg Gly Gln
        195                 200                 205
Gly Arg Val Pro Val Arg Glu Ser Pro His His Leu Ala Glu Ser
    210                 215                 220
Phe Leu Phe Leu Pro Gln Val Ser Pro Met Asp Ser Gly Pro Trp Gly
225                 230                 235                 240
Cys Ile Leu Thr Tyr Arg Asp Gly Phe Asn Val Ser Ile Met Tyr Asn
                245                 250                 255
Leu Thr Val Leu Gly Leu Glu Pro Pro Thr Pro Leu Thr Val Tyr Ala
            260                 265                 270
Gly Ala Gly Ser Arg Val Gly Leu Pro Cys Arg Leu Pro Ala Gly Val
        275                 280                 285
Gly Thr Arg Ser Phe Leu Thr Ala Lys Trp Thr Pro Pro Gly Gly Gly
    290                 295                 300
Pro Asp Leu Leu Val Thr Gly Asp Asn Gly Asp Phe Thr Leu Arg Leu
305                 310                 315                 320
Glu Asp Val Ser Gln Ala Gln Ala Gly Thr Tyr Thr Cys His Ile His
                325                 330                 335
Leu Gln Glu Gln Gln Leu Asn Ala Thr Val Thr Leu Ala Ile Ile Thr
            340                 345                 350
Val Thr Pro Lys Ser Phe Gly Ser Pro Gly Ser Leu Gly Lys Leu Leu
        355                 360                 365
Cys Glu Val Thr Pro Val Ser Gly Gln Glu Arg Phe Val Trp Ser Ser
    370                 375                 380
Leu Asp Thr Pro Ser Gln Arg Ser Phe Ser Gly Pro Trp Leu Glu Ala
385                 390                 395                 400
Gln Glu Ala Gln Leu Leu Ser Gln Pro Trp Gln Cys Gln Leu Tyr Gln
                405                 410                 415
Gly Glu Arg Leu Leu Gly Ala Ala Val Tyr Phe Thr Glu Leu Ser Ser
            420                 425                 430
Pro Gly Ala Gln Arg Ser Gly Arg Ala Pro Gly Ala Leu Pro Ala Gly
        435                 440                 445
His Leu Leu Leu Phe Leu Thr Leu Gly Val Leu Ser Leu Leu Leu Leu
    450                 455                 460
Val Thr Gly Ala Phe Gly Phe His Leu Trp Arg Arg Gln Trp Arg Pro
465                 470                 475                 480
Arg Arg Phe Ser Ala Leu Glu Gln Gly Ile His Pro Pro Gln Ala Gln
                485                 490                 495
Ser Lys Ile Glu Glu Leu Glu Gln Glu Pro Glu Pro Glu Pro Glu Pro
            500                 505                 510
Glu Pro Glu Pro Glu Pro Glu Pro Glu Gln Leu
        515                 520                 525

<210> SEQ ID NO 5
<211> LENGTH: 6
<212> TYPE: PRT
<213> ORGANISM: Mus musculus

<400> SEQUENCE: 5

Lys Ile Glu Glu Leu Glu
 1               5
```

```
<210> SEQ ID NO 6
<211> LENGTH: 8
<212> TYPE: PRT
<213> ORGANISM: Mus musculus
<220> FEATURE:
<221> NAME/KEY: VARIANT
<222> LOCATION: (1)...(8)
<223> OTHER INFORMATION: Xaa = Any Amino Acid

<400> SEQUENCE: 6

Gln Xaa Lys Ile Glu Glu Leu Glu
  1               5

<210> SEQ ID NO 7
<211> LENGTH: 11
<212> TYPE: PRT
<213> ORGANISM: Mus musculus

<400> SEQUENCE: 7

Ser Phe Glu Arg Phe Glu Ile Phe Pro Lys Glu
  1               5                  10

<210> SEQ ID NO 8
<211> LENGTH: 9
<212> TYPE: PRT
<213> ORGANISM: Mus musculus

<400> SEQUENCE: 8

Ile Tyr Ser Thr Val Ala Ser Ser Leu
  1               5

<210> SEQ ID NO 9
<211> LENGTH: 21
<212> TYPE: DNA
<213> ORGANISM: Mus musculus

<400> SEQUENCE: 9
acatcaacca gacagtggcc a                                              21

<210> SEQ ID NO 10
<211> LENGTH: 19
<212> TYPE: DNA
<213> ORGANISM: Mus musculus

<400> SEQUENCE: 10
gcatcccctg gtgaaggtc                                                 19

<210> SEQ ID NO 11
<211> LENGTH: 20
<212> TYPE: DNA
<213> ORGANISM: Mus musculus

<400> SEQUENCE: 11
cccactccca tcccggccct                                                20

<210> SEQ ID NO 12
<211> LENGTH: 20
<212> TYPE: DNA
<213> ORGANISM: Mus musculus

<400> SEQUENCE: 12
tgtatgaccc acccgaggtc                                                20
```

```
<210> SEQ ID NO 13
<211> LENGTH: 21
<212> TYPE: DNA
<213> ORGANISM: Mus musculus

<400> SEQUENCE: 13
ttaggatggt gccgttcttg t                                             21

<210> SEQ ID NO 14
<211> LENGTH: 26
<212> TYPE: DNA
<213> ORGANISM: Mus musculus

<400> SEQUENCE: 14
ccaatgccac attcaaagcc ctctcc                                        26

<210> SEQ ID NO 15
<211> LENGTH: 18
<212> TYPE: DNA
<213> ORGANISM: Mus musculus

<400> SEQUENCE: 15
tccggtgtgt tgcctgtg                                                 18

<210> SEQ ID NO 16
<211> LENGTH: 21
<212> TYPE: DNA
<213> ORGANISM: Mus musculus

<400> SEQUENCE: 16
caaagtctgc agtgaccgtc a                                             21

<210> SEQ ID NO 17
<211> LENGTH: 22
<212> TYPE: DNA
<213> ORGANISM: Mus musculus

<400> SEQUENCE: 17
catgggcacc ttctccgcag gt                                            22

<210> SEQ ID NO 18
<211> LENGTH: 28
<212> TYPE: DNA
<213> ORGANISM: Mus musculus

<400> SEQUENCE: 18
cattgaaagc ctagaaagtc tgaataac                                      28

<210> SEQ ID NO 19
<211> LENGTH: 21
<212> TYPE: DNA
<213> ORGANISM: Mus musculus

<400> SEQUENCE: 19
tggctctgca ggattttcat g                                             21

<210> SEQ ID NO 20
<211> LENGTH: 32
<212> TYPE: DNA
<213> ORGANISM: Mus musculus

<400> SEQUENCE: 20
tcaccatcct tttgccagtt cctccagtam ra                                 32
```

-continued

```
<210> SEQ ID NO 21
<211> LENGTH: 21
<212> TYPE: DNA
<213> ORGANISM: Mus musculus

<400> SEQUENCE: 21
cccaggaaag acagcaacct t                                              21

<210> SEQ ID NO 22
<211> LENGTH: 21
<212> TYPE: DNA
<213> ORGANISM: Mus musculus

<400> SEQUENCE: 22
ttctcacaac caggccactt g                                              21

<210> SEQ ID NO 23
<211> LENGTH: 28
<212> TYPE: DNA
<213> ORGANISM: Mus musculus

<400> SEQUENCE: 23
atcctaccca ctgctggcaa atggagtc                                       28
```